United States Patent
Burk

(10) Patent No.: US 6,602,900 B2
(45) Date of Patent: *Aug. 5, 2003

(54) CYCLOPENTANE HEPTAN(ENE)OIC ACID, 2-HETEROARYLALKENYL DERIVATIVES AS THERAPEUTIC AGENTS

(75) Inventor: Robert M. Burk, Laguna Beach, CA (US)

(73) Assignee: Allergan, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/021,485

(22) Filed: Oct. 29, 2001

(65) Prior Publication Data

US 2002/0198249 A1 Dec. 26, 2002

Related U.S. Application Data

(60) Continuation-in-part of application No. 09/795,982, filed on Feb. 28, 2001, now Pat. No. 6,310,087, which is a continuation of application No. 09/523,880, filed on Mar. 13, 2000, now Pat. No. 6,204,287, which is a continuation of application No. 09/295,003, filed on Apr. 20, 1999, now Pat. No. 6,037,364, which is a continuation of application No. 09/185,403, filed on Nov. 3, 1998, now Pat. No. 5,972,991, which is a continuation-in-part of application No. 08/726,921, filed on Oct. 7, 1996, now Pat. No. 5,834,498, which is a continuation-in-part of application No. 08/605,567, filed on Feb. 22, 1996, now Pat. No. 5,688,819, which is a continuation-in-part of application No. 08/371,339, filed on Jan. 11, 1995, now Pat. No. 5,607,978, which is a continuation of application No. 08/154,244, filed on Nov. 18, 1993, now abandoned, which is a division of application No. 07/948,056, filed on Sep. 21, 1992, now Pat. No. 5,352,708.

(51) Int. Cl.[7] .................. C07D 333/16; A61K 31/38
(52) U.S. Cl. .................. 514/438; 514/365; 548/204; 549/58; 549/77; 549/79; 549/501
(58) Field of Search .................. 548/204; 514/365, 514/438; 549/58, 77, 79, 501

(56) References Cited

U.S. PATENT DOCUMENTS

| 5,296,504 A | 3/1994 | Stjernschantz et al. |
| 5,321,128 A | 6/1994 | Stjernschantz et al. |
| 5,422,368 A | 6/1995 | Stjernschantz et al. |
| 5,422,369 A | 6/1995 | Stjernschantz et al. |
| 6,037,364 A | 3/2000 | Burk |

FOREIGN PATENT DOCUMENTS

| EP | 0 603 800 | 6/1994 |
| GB | 1446341 A | 8/1976 |
| WO | 90 02553 | 3/1990 |
| WO | 94 06433 | 3/1994 |

OTHER PUBLICATIONS

C. Liljebris et al, *Derivatives of 17–Phenyl–18, 19, 20–trinorprostaglandin F–2–alpha Isopropyl Esters: Potential Antiglaucoma Agents*, J. Med. Chem. vol. 38, No. 2, Jan. 20, 1995, pp. 289–304.

Primary Examiner—Robert Gerstl
(74) Attorney, Agent, or Firm—Robert J. Baran; Martin A. Voet; Carlos A. Fisher

(57) ABSTRACT

The invention relates to the use of derivatives of F-type prostaglandins as ocular hypotensives. The PGF derivatives used in accordance with the invention are represented by the following formula I:

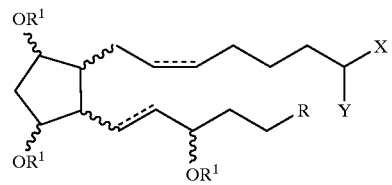

wherein wavy line attachments indicate either the alpha ($\alpha$) or beta ($\beta$) configuration; dashed bonds represent a double bond, or a single bond, R is a substituted heteroaryl radical, $R^1$ is hydrogen or a lower alkyl radical having up to six carbon atoms, X is selected from the group consisting of —$OR^1$, —$N(R^1)_2$, $R^1$ is hydrogen or a lower alkyl radical having up to six carbon atoms, X is selected from the group consisting of —$OR^1$, —$N(R^1)_2$ and —$N(R^5)SO_2R^6$, wherein $R^5$ represents hydrogen or $CH_2OR^6$ and $R^6$ represents hydrogen or a lower alkyl radical having up to six carbon atoms and halogen substituted derivatives of said lower alkyl radical, e.g. a fluoro substituted lower alkyl radical; Y is =O or represents 2 hydrogen radicals. Certain of the compounds represented by Formula I comprise another aspect of the present invention.

17 Claims, 5 Drawing Sheets

3p α-OH
3q β-OH
3r α-OH

↓ PPTS, MeOH, 40°C

7p α-OH
7q β-OH
7r α-OH

↓ NH₄Cl
NH₃
55-60°C

8p α-OH
8q β-OH
8r α-OH

2k

↓ ALIQUAT 336
Na₂S₂O₄
NaHCO₃
BENZENE:H₂O, 80°C

14

↓ 1. NaBH₄, MeOH
2. PPTs, MeOH, 45°C
3. 0.5 N LiOH IN THF

15

CYCLOPENTANE HEPTAN(ENE)OIC ACID, 2-HETEROARYLALKENYL DERIVATIVES AS THERAPEUTIC AGENTS

CROSS-REFERENCES TO RELATED APPLICATIONS

This patent application is a continuation in part of Ser. No. 09/795,982, which was filed on Feb. 28, 2001, now U.S. Pat. No. 6,310,087; which is a continuation of U.S. Ser. No. 09/523,880, which was filed on Mar. 13, 2000, now U.S. Pat. No. 6,204,287; which is a continuation of Ser. No. 09/295,003, which was filed on Apr. 20, 1999, now U.S. Pat. No. 6,037,364; which is a continuation of U.S. Ser. No. 09/185,403 which was filed on Nov. 3, 1998, now U.S. Pat. No. 5,972,991; which is a continuation-in-part of U.S. Ser. No. 08/726,921, which was filed on Oct. 7, 1996, now U.S. Pat. No. 5,834,498; which is continuation-in-part of U.S. Ser. No. 08/605,567 filed on Feb. 22, 1996, now U.S. Pat. No. 5,688,819; which is a continuation-in-part of U.S. Ser. No. 08/371,339 which was filed on Jan. 11, 1995, now U.S. Pat. No. 5,607,978; which is a continuation of U.S. Ser. No. 08/154,244 which was filed Nov. 18, 1993, now abandoned; which is a divisional of U.S. Ser. No. 07/948,056 filed Sep. 21, 1992, now U.S. Pat. No. 5,352,708.

BACKGROUND OF THE INVENTION

1. Field of the Invention

The present invention relates to cyclopentane heptanoic acid, 2 heteroarylalkenyl derivatives which may be substituted in the 1-position with hydroxyl, alkyloxy, amino and amido groups, e.g. 1-OH cyclopentane heptanoic acid, 2 heteroarylalkenyl derivatives. These compounds are potent ocular hypotensive and are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

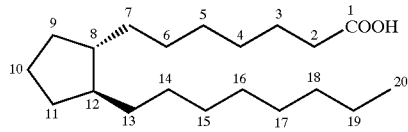

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [[e.g. prostaglandin $F_{2\alpha}$ ($PGF_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins,* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrug* 53 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175,476 (filed Dec. 29, 1993). Similarly, 11,15-9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed Jul. 7, 1989, now U.S. Pat. No. 4,994,274), Ser. No. 584,370 (filed Sep. 18, 1990, now U.S. Pat. No. 5,028,624) and Ser. No. 585,284 (filed Sep. 18, 1990, now U.S. Pat. No. 5,034,413). The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I

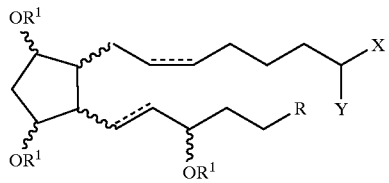

wherein the wavy segments represent an α or β bond, dashed lines represent a double bond or a single bond, R is a substituted heteroaryl radical, $R^1$ is hydrogen or a lower alkyl radical having up to six carbon atoms, X is selected from the group consisting of $-OR^1$, $-N(R^1)_2$, and $-N(R^5)SO_2R^6$, wherein $R^5$ represents hydrogen or $CH_2OR^6$ and $R^6$ represents hydrogen or a lower alkyl radical having up to six carbon atoms and halogen substituted derivatives of said lower alkyl radical, e.g. a fluoro substituted lower alkyl radical; Y is =O or represents 2 hydrogen radicals, and 1, 9, 11 or 15 esters thereof.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application. In particular, the substituents on the heteroaryl radical may be selected from the group consisting of lower alkyl, e.g. $C_1$ to $C_6$ alkyl; halogen, e.g. fluoro, chloro and bromo; trifluoromethyl ($CF_3$); $COR^1$, e.g. $COCH_3$; $COCF_3$; $SO_2NR^1$, e.g. $SO_2NH_2$; $NO_2$; CN; etc.

In a still further aspect, the present invention relates to a pharmaceutical product, comprising
  a container adapted to dispense its contents in a metered form; and
  an ophthalmic solution therein, as hereinabove defined.

Finally, certain of the compounds represented by the above formula, disclosed below and utilized in the method of the present invention are novel and unobvious.

BRIEF DESCRIPTION OF THE DRAWING FIGURES

DETAILED DESCRIPTION OF THE INVENTION

Figure 1:
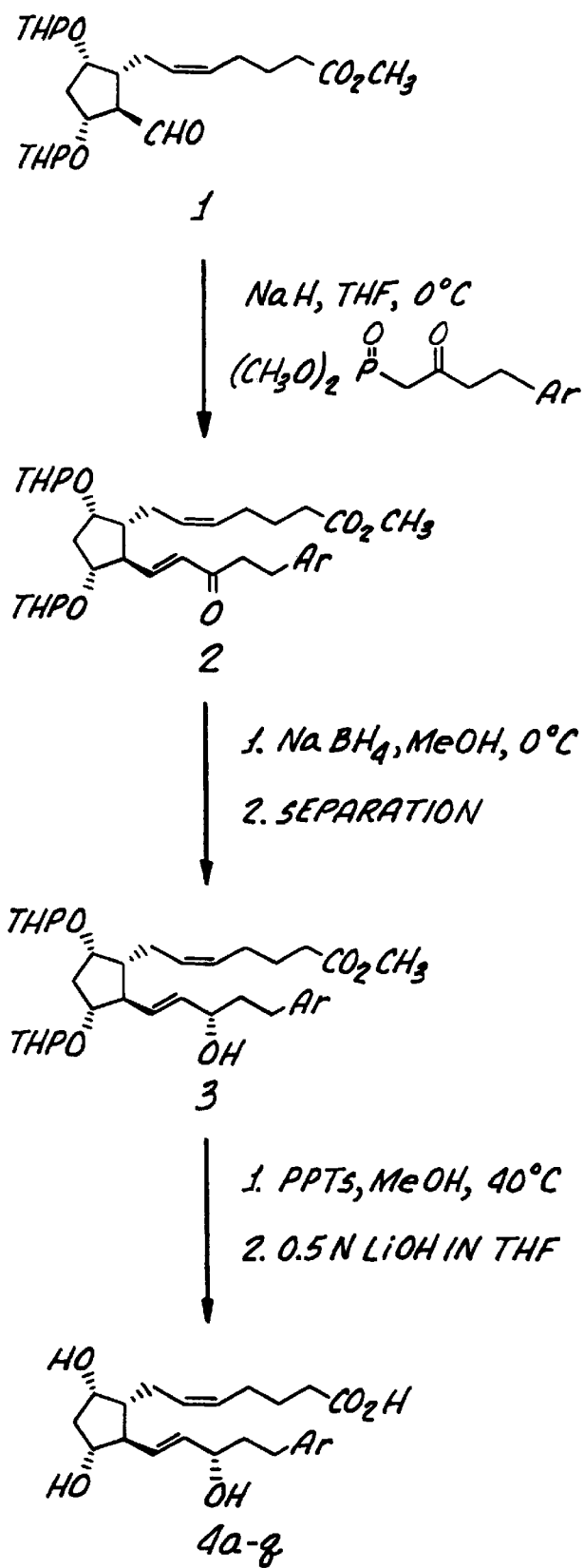
FIG. 1 is a schematic of the chemical synthesis of certain 1-carboxylic acid compounds of the invention specifically disclosed as Example 4(a)–(v) below.

The present invention relates to the use of cyclopentane heptan(ene)oic acid, 2-heteroaryl alkenyl derivatives as therapeutic agents, e.g. as ocular hypotensives. The compounds or derivatives used in accordance with the present invention are encompassed by the above structural formula I:

Preferably said compounds are represented by formula II:

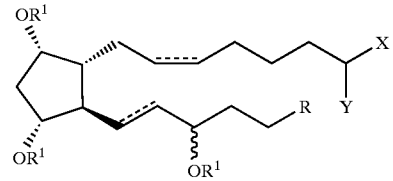

wherein the substituents and symbols are as hereinabove defined. The dotted lines on bonds between carbons 5 and 6 (C-5) and carbons 13 and 14 (C-13) indicate a single or double bond. If two solid lines are used at C-5, or C-13, it indicates a specific configuration for that double bond. Hatched lines used at position C-8, C-9 and C-11 indicate the α configuration. A triangle at position C-12 represents β orientation. A more preferred group of the compounds of the present invention includes compounds that have the following structural formula III:

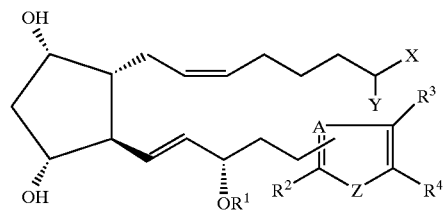

wherein Z is selected from the group consisting of O and S, A is selected from the group consisting of N, —CH, and C, $R^2$ is selected from the group consisting of hydrogen, halogen, and lower alkyl having from 1 to 6 carbon atoms, $R^3$ and $R^4$ are selected from the group consisting of hydrogen, halogen, lower alkyl having from 1 to 6 carbon atoms, or, together with

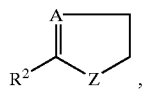

R³ and R⁴ forms a condensed aryl ring. Preferably, when X is —N(R¹)₂, Y is =O.

More preferably, at least one of R², R³ or R⁴ are independently selected from the group consisting of chloro, bromo and lower alkyl. In one aspect of the invention, at least one of R², R³ or R⁴ is chloro or bromo, and more preferably at least one of R², R³ or R⁴ is bromo or at least two of R², R³ or R⁴ are chloro. In another aspect of this invention, at least one of R², R³ or R⁴ is ethyl, propyl, or butyl.

Preferably R⁵ is hydrogen or CH₂OH, wherein the OH group is esterified with acetic acid or pivalic acid, i.e. R⁵ is

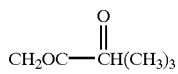

or

Preferably R6 is methyl, ethyl or trifluoromethyl.

Another preferred group includes compounds having the formula IV:

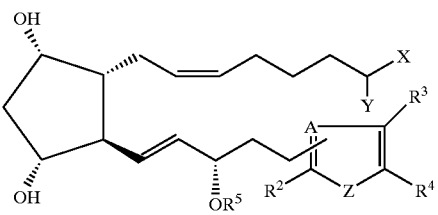

In the above formulae, the substituents and symbols are as hereinabove defined and R⁵ is hydrogen or methyl.

The above compounds of the present invention may be prepared by methods that are known in the art or according to the working examples below. The compounds, below, are especially preferred representative of the compounds of the present invention.

7-[3α,5α-Dihydroxy-2-(3α-hydroxy-5-(3-(2-methyl)-thienyl-1E-pentenyl)cyclopentyl]-5Z-heptenoic acid 7-[3α,5α-Dihydroxy-2-(3α-hydroxy-5-(4-(2-methyl)-thienyl-1E-pentenyl)cyclopentyl]-5Z-heptenoic acid 7-[3α,5α-Dihydroxy-2-(3α-hydroxy-5-(2-(5-methyl)thienyl)-1E-pentenyl)cyclopentyl]-5Z-heptenoic acid.

7-[3α,5α-Dihydroxy-2-(3α-hydroxy-5-(3-(2-chloro)thienyl)-1E-pentenyl)cyclopentyl]-5Z-heptenoic acid.

7-[3α,5α-Dihydroxy-2-(3α-hydroxy-5-(2-(4-bromo)thienyl)-1E-pentenyl)cyclopentyl]-5Z-heptenoic acid.

7-[3α,5α-Dihydroxy-2-(3α-hydroxy-5-(2-(5-bromo)thienyl)-1E-pentenyl)cyclopentyl]-5Z-heptenoic acid.

7-[3α,5α-Dihydroxy-2-(3α-hydroxy-5-(3-(2,5-dichloro)thienyl)-1E-pentenyl)cyclopentyl]-5Z-heptenoic acid.

7-[3α,5α-Dihydroxy-2-(3α-hydroxy-5-(2-(3-chloro)thienyl)-1E-pentenyl)cyclopentyl]-5Z-heptenoic acid.

7-[3α,5α-Dihydroxy-2-(3α-hydroxy-5-(2-benzothienyl)-1E-pentenyl)cyclopentyl]-5Z-heptenoic acid.

7-[3α,5α-Dihydroxy-2-(3α-hydroxy-5-(2-benzofuranyl)-1E-pentenyl)cyclopentyl]-5Z-heptenoic acid 7-[3α,5α-Dihydroxy-2-(3α-hydroxy-5-(2-(3-furanyl)-1E-pentenyl)cyclopentyl]-5Z-heptenoic acid.

7-[3α,5α-Dihydroxy-2-(3α-hydroxy-5-(2-furanyl)-1E-pentenyl)cyclopentyl]-5Z-heptenoic acid.

7-[3α,5α-Dihydroxy-2-(3α-hydroxy-5-(2-thiazolyl)-1E-pentenyl)cyclopentyl]-5Z-heptenoic acid.

7-[3α,5α-Dihydroxy-2-(3α-hydroxy-5-(2-(thienyl)-1E-pentenyl)cyclopentyl]-5Z-heptenoic acid.

7-[3α,5α-Dihydroxy-2-(3β-hydroxy-5-(2-thienyl)-1E-pentenyl)cyclopentyl]-5Z-heptenoic acid.

7-[3α,5α-Dihydroxy-2-(3α-hydroxy-5-(3-thienyl)-1E-pentenyl)cyclopentyl]-5Z-heptenoic acid.

7-[3α,5α-Dihydroxy-2-(3α-hydroxy-5-(3-(2,5-dichloro)thienyl-1E-pentenyl)cyclopentyl]-5Z-heptenamide.

7-[3α,5α-Dihydroxy-2-(3β-hydroxy-5-(3-thienyl)-1E-pentenyl)cyclopentyl]-5Z-heptenoic acid.

7-[3α,5α-Dihydroxy-2-(3α-hydroxy-5-(3-thienyl)-1E-pentenyl)cyclopentyl]-5Z-heptenoic acid.

7-[3α,5α-Dihydroxy-2-(3α-methoxy-5-(3-thienyl)-1E-pentenyl)cyclopentyl]-5Z-heptenoic acid.

7-[3α,5α-Dihydroxy-2-(3α-hydroxy-5-(3-thienyl)-1E-pentenyl)cyclopentyl]-5Z-heptenamide.

7-[3α,5α-Dihydroxy-2-(3β-hydroxy-5-(3-thienyl)-1E-pentenyl)cyclopentyl]-5Z-heptenamide.

7-[3α,5α-Dihydroxy-2-(3-hydroxy-5-(2-(3,4 dibromo)thienyl-1E-pentenyl)cyclopentyl]-5-Z-heptenoic acid.

(7-[3α,5α-Dihydroxy-2-(3-hydroxy-5-(2-(5-iodo)thienyl)-1E-pentenyl)cyclopentyl]-5Z-heptenoic acid.

(7-[3α,5α-Dihydroxy-2-(3-hydroxy-5-(2-(4-bromo, 5 methyl)thienyl)-1E-pentenyl)cyclopentyl]-5Z-heptenoic acid.

(7-[3α,5α-Dihydroxy-2-(3-hydroxy-5-(2-(3,5-dibromo)thienyl)-1E-pentenyl)cyclopentyl]-5Z-heptenoic acid.

(7-[3α,5α-Dihydroxy-2-(3-hydroxy-5-(2-(3,4 dibromo-5 methyl)thienyl)-1E-pentenyl)cyclopentyl]-5Z-heptenoic acid.

(7-[3α,5α-Dihydroxy-2-(3-hydroxy-5-(2-(4 chloro-5 methyl)thienyl)-1E-pentenyl)cyclopentyl]-5Z-heptenoic acid.

(7-[3α,5α-Dihydroxy-2-(3-hydroxy-5-(2-(2 methyl)thienyl)-1E-pentenyl)cyclopentyl]-5Z-heptenoic acid.

7-[3α,5α-Dihydroxy-2-(3α-hydroxy-5-(3-iodo) 2-thienyl) 1E-pentyl)cyclopentyl]-5Z-heptenamide.

7-[3α,5α-Dihydroxy-2-(3α-hydroxy-5-(3-methyl 4 bromo) 2-thienyl)1E-pentyl)cyclopentyl]-5Z-heptenamide.

7-[3α,5α-Dihydroxy-2-(3α-hydroxy-5-(3,4 dibromo )2-thienyl)1E-pentyl)cyclopentyl]-5Z-heptenamide.

7-[3α,5α-Dihydroxy-2-(3α-hydroxy-5-(3-methyl,4,5 dibromo)-2-thienyl)1E-pentyl)cyclopentyl]-5Z-heptenamide.

7-[3α,5α-Dihydroxy-2-(3α-hydroxy-5-(3-methyl,4 chloro)-2-thienyl)1E-pentyl)cyclopentyl]-5Z-heptenamide.

7-[3α,5α-Dihydroxy-2-(3α-hydroxy-5-(5-methyl 2-thienyl) 1-E-pentenyl)cyclopentyl]-5Z-heptenamide.

A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Figure 2:
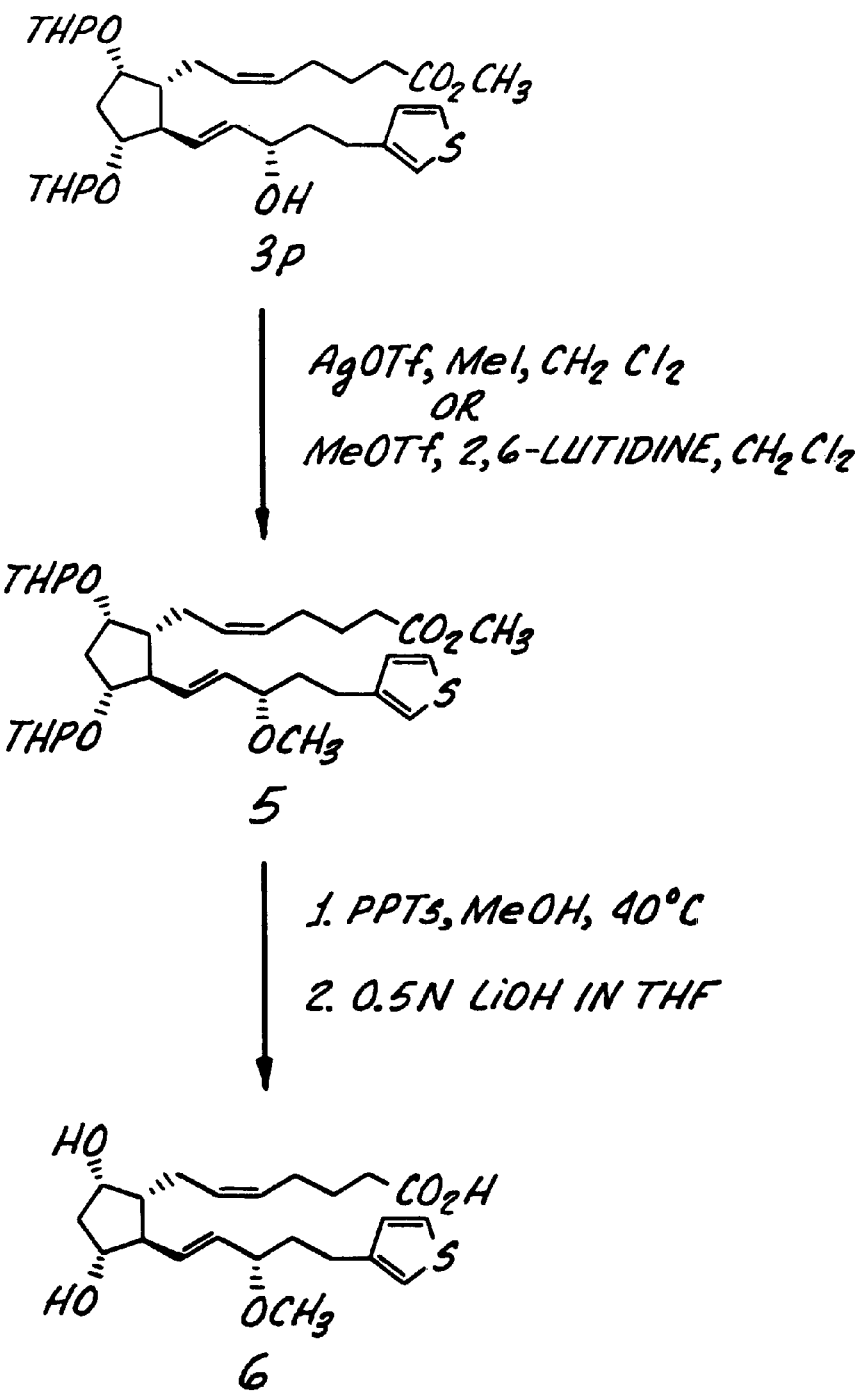
FIG. 2 is a schematic of the chemical synthesis of certain δ-substituted thienyl 1-carboxylic acid compound of the invention specifically disclosed as Examples 6 and 6(a), below.
Figure 3:
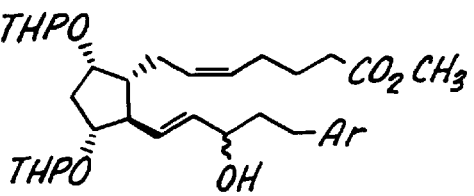
FIG. 3 is a schematic of the chemical synthesis of certain 1-amido compounds of the invention specifically disclosed as Examples 8(p)–(q), below.
Figure 3:
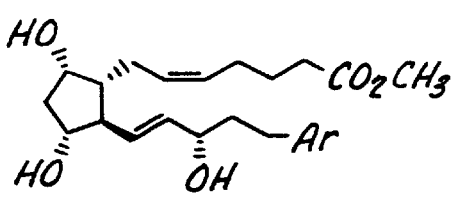
Figure 3:
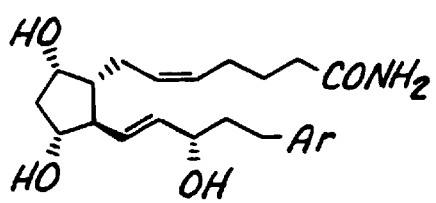
Figure 4:
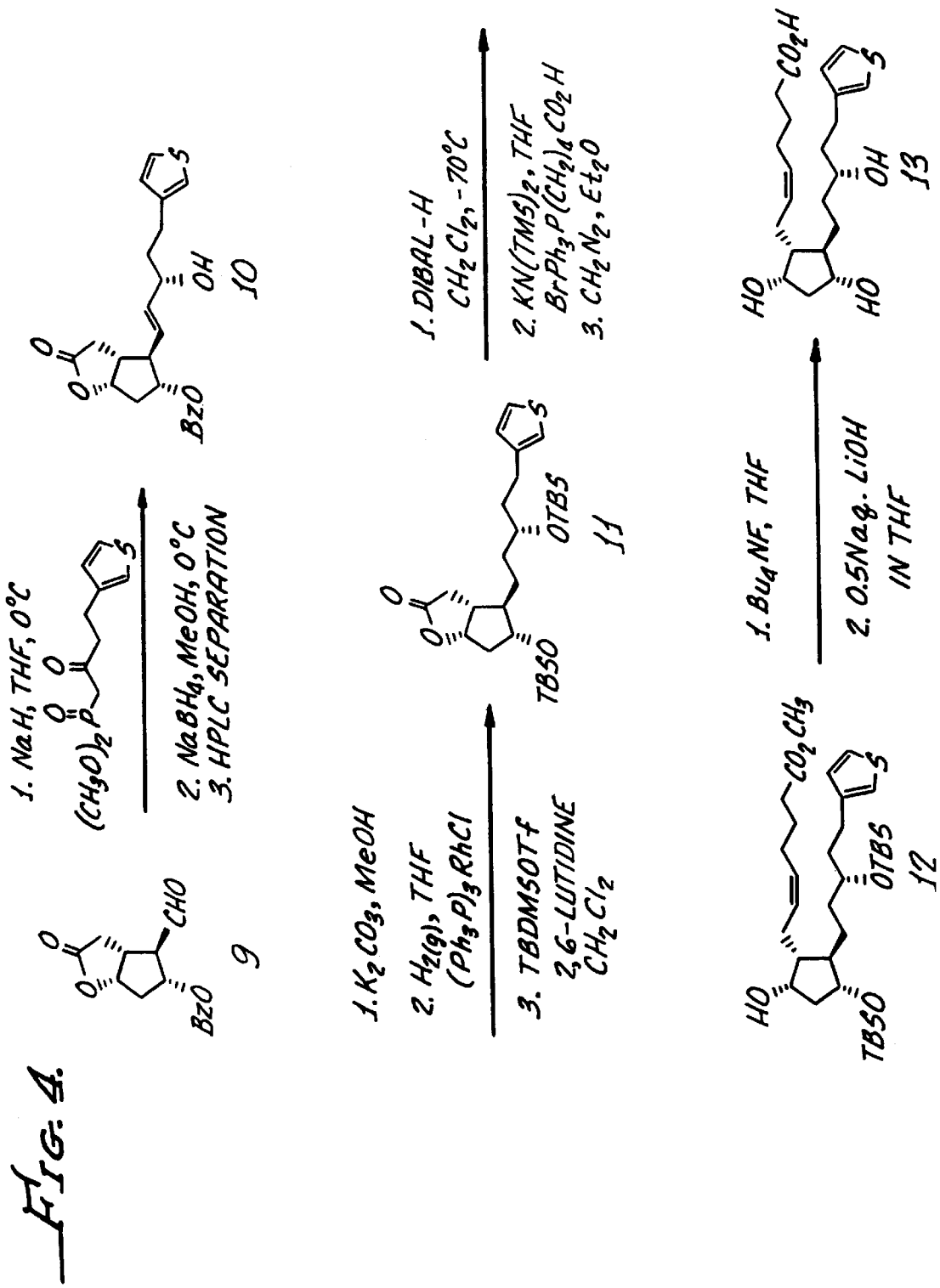
FIG. 4 is a schematic of the chemical synthesis of certain-substituted thienyl 1-carboxylic acid compounds.
Figure 5:
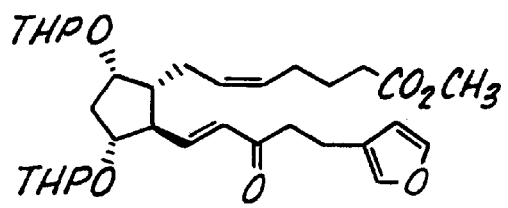
FIG. 5 is a schematic of the chemical synthesis of δ-substituted furanyl-1-carboxylic acid compounds specifically disclosed as Example 15.
Figure 5:
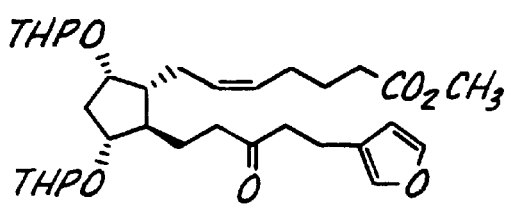
Figure 5:
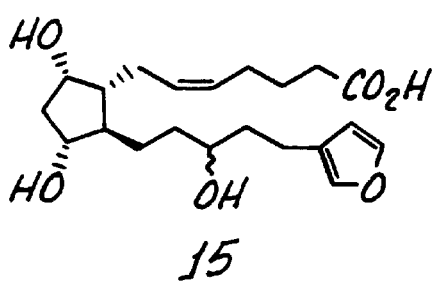

The invention is further illustrated by the following non-limiting Examples, which are summarized in the reaction schemes of FIGS. 1 through 4, wherein the compounds are identified by the same designator in both the Examples and the Figures.

Compound 4a

7-[3α,5α,-Dihydroxy-2-(3α-hydroxy-5-(3-(2-methyl)thienyl-1E-pentenyl)cyclopentyl]-5Z-heptenoic acid Step 1: Preparation of Enone 2a To a suspension of sodium hydride (36 mg, 1.50 mmol) in THF (4.5 mL) cooled to 0° C. was added dimethyl 4-(3-(2-methyl) thienyl)-2-oxo-butylphosphonate(414 mg, 1.50 mmol) in THF (3.0 mL). After 0.25 h a solution of the aldehyde 1 (438 mg, 1.00 mmol) in THF (3.0 mL) was added and the reaction was allowed to slowly warm to 23° C. over a period of 8 h. The reaction solution was quenched with saturated aqueous $NH_4Cl$ and extracted w/EtOAc. The aqueous phase was made slightly acidic before extraction with EtOAc. The combined organics were washed with brine, dried ($MgSO_4$), filtered and concentrated in vacuo. Flash column chromatography (silica gel, 2:1 hex/EtOAc) gave 544 mg (93%) of the enone 2a.

Step 2: Preparation of alcohol 3a

Sodium tetrahydriodoborate (35 mg, 0.93 mmol) was added to a solution of the enone 2a (544 mg, 0.93 mmol) in MeOH(4.5 mL) at 0° C. After 2 h the solvent was removed in vacuo and the residue was stirred with 1N NaOH/EtOAc. The organic portion was separated, dried ($MgSO_4$), filtered and concentrated in vacuo. The 3a-alcohol was separated by flash column chromatography or HPLC (silica gel, 3:1 Hex/EtOAc).

Step 3: Preparation of 7-[3α,5α-Dihydroxy-2-(3α-hydroxy-5-(3-(2-methyl)thienyl-1E-pentenyl) cyclopentyl]-5Z-heptenoic acid A solution of alcohol 3a and pyridinium p-toluene sulfonate (116 mg, 0.462 mmol) in MeOH(4.5 mL) was heated at 40° C. for 4 h. The solvent was removed in vacuo and the residue was diluted with EtOAc followed by washing with 1N HCl, saturated aqueous $NaHCO_3$ and brine. The organic portion was dried ($MgSO_4$), filtered and concentrated in vacuo.

The residue was diluted with THF (0.78 mL) and lithium hydroxide (0.39 mL of a 0.5N solution in $H_2O$, 0.194 mmol) was added. After 16 h the reaction was acidified with IN HCl and extracted with EtOAc. The organic portion was washed with brine, dried ($MgSO_4$), and concentrated in vacuo to give 37.6 mg of the free acid 4a.

The title compound was identified by the following NMR spectrum. $^1H$ NMR (300 $MH_2$, $CDCl_3$) δ12.1(brs, 1H), 6.98 (d, J=5.1 Hz), 6.81(d, J=5.1 Hz, 1H), 5.30–5.64(m, 4H), 4.92(brs, 3H), 4.07–4.17 (m, 2H), 3.89–3.93(m, 1H), 2.55–2.59 (m, 2H), 2.35(δ, 3H), 2.07–2.33(m, 10H), 1.42–1.86(m, 4H).

By methods described for compound 4a, steps 1 through 3, the following compounds were prepared. (The compounds below are also identified by their NMR spectra.)

Compound 4b

7-[3α,5α-Dihydroxy-2-(3α-hydroxy-5-(2-(5-methyl)thienyl)-1E-pentenyl)cyclopentyl]-5Z-heptenoic acid According to the procedures described above for 4a, the use of dimethyl 4-(2-(5-methyl)thienyl)-2-oxo-butylphosphonate afforded 26 mg of free acid 4b.

$^1$H NMR (300 MH$_2$, CDCl$_3$) δ12.1(brs, 1H), 6.56 (d, J=3.4 Hz, 1H), 6.54(d, J=3.4 Hz, 1H), 5.34–5.64(m, 4H), 4.70(brs, 3H), 4.13–4.20 (m, 2H), 3.91–393(m, 1H), 2.82 (t, J=7.7 Hz, 2H), 2.42(δ, 3H), 2.05–2.38(m, 11H), 1.44–1.96 (m, 5H).

Compound 4c

7-[3α,5α-Dihydroxy-2-(3α-hydroxy-5-(3-(5-methyl)thienyl)-1E-pentynyl)cyclopentyl]-5Z-heptenoic acid According to the procedures described above for 4a, the use of dimethyl 4-(3-(2-methyl)thienyl)-2-oxo-butyl phosphonate afforded 25 mg of free acid 4c.

$^1$H NMR (300 MH$_2$, CDCl$_3$) δ12.0(brs, 1H), 6.67 (s, 1H), 6.60(s, 1H), 5.34–5.62(m, 4H), 4.42(brs, 3H), 4.10–4.17 (m, 2H), 3.89–3.93(m, 1H), 2.57–2.60(m, 2H), 2.44(δ, 3H), 2.09–2.36(m, 8H), 1.44–1.87(m, 6H).

Compound 4d

7-[3α,5α-Dihydroxy-2-(3α-hydroxy-5-(3-(2-chloro)thienyl)-1E-pentynyl)cyclopentyl]-5Z-heptenoic acid According to the procedures described above for 4a, the use of dimethyl 4-(3-(2-chloro)thienyl)-2-oxo-butylphosphonate afforded 25 mg of free acid 4d.

$^1$H NMR (300 MH$_2$, CDCl$_3$) δ12.0(brs, 1H), 6.99 (d, J=5.7H$_2$), 6.78(d, J=5.7 Hz, 1H), 5.29–5.60(m, 4H), 4.02–4.11 (m, 2H), 3.84–3.87(m, 1H), 3.37(brs, 3H), 2.56–2.63(m, 2H), 2.01–2.32(m, 8H), 1.38–1.83(m, 7H).

Compound 4e

7-[3α,5α-Dihydroxy-2-(3α-hydroxy-5-(2-(4-bromo)thienyl)-1E-pentenyl)cyclopentyl]-5Z-heptenoic acid According to the procedures described above for 4a, the use of dimethyl 4-(2-(4-bromo)thienyl)-2-oxo-butylphosphonate afforded 10 mg of free acid 4e.

$^1$H NMR (300 MH$_2$, CDCl$_3$) δ12.01(brs, 1H), 6.95 (s, 1H), 6.65(s, 1H), 5.24–5.53(m, 4H), 3.99–4.08 (m, 2H), 3.76–3.80(m, 1H), 2.70–2.79(m, 2H), 2.44(s, 3H), 2.09–2.36(m, 8H), 1.44–1.87(m, 6H).

Compound 4f

7-[3α,5α-Dihydroxy-2-(3α-hydroxy-5-(2-(5-bromo)thienyl)-1E-pentenyl)cyclopentyl]-5Z-heptenoic acid According to the procedures described above for 4a, the use of dimethyl 4-(2-(5-bromo)thienyl)-2-oxo-butylphosphonate afforded 50 mg of free acid 4f.

$^1$H NMR (300 MH$_2$, CDCl$_3$) δ12.0(brs, 1H), 6.80 (d, J=3.6 Hz, 1H), 6.51(d, J=3.9 Hz, 1H), 5.33–5.55(m, 4H), 4.05–4.12(m, 2H), 3.82–3.88(m, 1H), 2.75–2.81(m, 2H), 1.38–2.28 (m, 14H).

Compound 4g

7-[3α,5α-Dihydroxy-2-(3α-hydroxy-5-(3-(2,5-dichloro)thienyl)-1E-pentenyl)cyclopentyl]-5Z-heptenoic acid According to the procedures described above for 4a, the use of dimethyl 4-(3-(2,5-dichloro)thienyl)-2-oxo-butylphosphonate afforded 18 mg of free acid 4g.

$^1$H NMR (300 MHz, CDCl$_3$) δ12.01(brs, 1H), 6.64 (s, 1H), 5.27–5.56(m, 4H), 4.05–4.15(m, 2H), 3.85–3.92(m, 1H), 1.42–2.31(m, 18H).

Compound 4h

7-[3α,5α-Dihydroxy-2-(3α-hydroxy-5-(2-(3-chloro)thienyl)-1E-pentenyl)cyclopentyl]-5Z-heptenoic acid According to the procedures described above for 4a, the use of dimethyl 4-(2-(3-chloro)thienyl)-2-oxo-butylphosphonate afforded 10 mg of free acid 4h.

$^1$H NMR (300 MHz, CDCl$_3$) δ12.0(brs, 1H), 7.13 (d, J=5.4 Hz, 1H), 6.75(d, J=5.4 Hz, 1H), 5.19–5.46(m, 4H), 3.96–3.98(m, 2H), 3.69–3.76(m, 1H), 2.72–2.75(m, 2H), 1.35–2.28(m, 17H).

Compound 4i

7-[3α,5α-Dihydroxy-2-(3α-hydroxy-5-(2-benzothienyl)-1-E-pentenyl)cyclopentyl]-5Z-heptenoic acid According to the procedures described above for 4a, the use of dimethyl 4-(2-benzothienyl)-2-oxo-butylphosphonate afforded 22 mg of free acid 4i.

$^1$H NMR (300 MHz, CDCl$_3$) δ11.8(brs, 1H), 7.73(d, J=7.7 Hz, 1H), 7.63(d, J=6.9 Hz, 1H), 7.23–7.31(m, 2H), 7.00(s, 1H), 5.31–5.65(m, 4H), 4.86(brs, 3H), 4.16–4.22 (m, 2H), 3.89–3.93(m, 1H), 2.96 (t, J=7.6 Hz, 2H)1.86–2.35(m, 10H), 1.44–1.78(m, 4H).

Compound 4j

7-[3α,5α-Dihydroxy-2-(3α-hydroxy-5-(2-benzofuranyl)-1E-pentenyl)cyclopentyl]-5Z-heptenoic acid According to the procedures described above for 4a, the use of dimethyl 4-(2-benzofuranyl)-2-oxo-butylphosphonate afforded 30.5 mg of free acid 4j.

$^1$H NMR (300 MHz, CDCl$_3$) δ12.1(brs, 1H), 7.37–7.47 (m, 2H), 7.15–7.19(m, 2H), 6.38(s, 1H), 5.30–5.66 (m, 4H), 5.04 (brs, 3H), 4.10–4.20(m, 2H), 3.86–3.94(m, 1H), 2.84(t, J=7.6 Hz, 2H)1.90–2.33(m, 10 H), 1.38–1.78(m, 4H).

Compound 4k

7-[3α,5α-Dihydroxy-2-(3α-hydroxy-5-(2-(3-furanyl)-1E-pentenyl)cyclopentyl]-5Z-heptenoic acid According to the procedures described above for 4a, the use of dimethyl 4-(3-furanyl)-2-oxo-butylphosphonate afforded 10.1 mg of free acid 4k.

1H NMR (300 MH$_2$, CDCl$_3$) δ12.0(brs, 1H), 7.35 (d, J=1.7 Hz, 1H), 7.23(s, 1H), 6.28 (d, J=1.7 Hz, 1H), 5.34–5.64(m, 4H), 4.15–4.20(m, 2H), 3.90–3.94 (m, 1H), 3.70 (brs, 3H), 2.09–2.52 (m, 12H), 1.40–1.88 (m, 4H).

Compound 4l

7-[3α,5α-Dihydroxy-2-(3α-hydroxy-5-(2-furanyl)-1E-pentenyl)cyclopentyl]-5Z-heptenoic acid According to the procedures described above for 4a, the use of dimethyl 4-(2-furanyl)-2-oxo-butylphosphonate afforded 33.3 mg of free acid 4l.

$^1$H NMR (300 MHz, CDCl$_3$) δ11.8(brs, 1H), 7.29(s, 1H), (d, J=3.0 Hz 1H), 6.26(dd, J=3.0, 1.8 Hz, 1H), 5.99 (d, J=1.8

Hz, 1H) 5.34–5.64 (m, 4H), 4.82 (brs, 3H), 4.11–4.17 (m, 2H), 3.89–3.93 (m, 1H), 2.69 (t, J=8.4 Hz, 2H), 2.05–2.34 (m, 10H), 1.40–1.94(m, 4H).

Compound 4m

7-[3α,5α-Dihydroxy-2-(3α-hydroxy-5-(2-thiazolyl)-1E-pentenyl)cyclopentyl]-5Z-heptenoic acid According to the procedures described above for 4a, the use of dimethyl 4-(2-thiazolyl)-2-oxo-butylphosphonate afforded 32.2 mg of free acid 4m.

$^1$H NMR (300 MHz, CD$_3$OD) δ7.47 (d, J=3.3 Hz, 1H), 7.23(d, J=3.3 Hz, 1H), 3.86–3.93 (m, 2H), 3.60–3.65 (m, 1H), 2.88–2.95 (m, 2H), 1.75–2.20 (m, 10H), 122–1.44(m, 4H).

Compound 4n

7-[3α,5α-Dihydroxy-2-(3α-hydroxy-5-(2-(thienyl)-1E-pentenyl)cyclopentyl]-5Z-heptenoic acid According to the procedures described above for 4a, the use of dimethyl 4-(2-thienyl)-2-oxo-butylphosphonate afforded 15.0 mg of free acid 4n.

$^1$H NMR (300 MHz, CDCl$_3$) δ11.9(brs, 1H), 7.11, (d, J=5.1 Hz, 1H), 6.92(dd, J=5.1, 3.3 Hz, 1H), 6.00 (d, J=3.3 Hz, 1H) 5.32–5.64 (m, 4H), 4.15–4.19(m, 2H), 3.93–3.97 (m, 1H), 3.61 (brs, 3H), 2.89–2.95 (m, 2H), 2.09–2.35 (m, 8H), 1.46–1.98(m, 6H).

Compound 4o

7-[3α,5α-Dihydroxy-2-(3α-hydroxy-5-(2-thienyl)-1E-pentenyl)cyclopentyl]-5Z-heptenoic acid The 3β-isomer of 3n was isolated from the reaction mixture obtained in step 2 during preparation of 4n and subjected to step 3 to afford 14.3 mg of free acid 4o.

$^1$H NMR (300 MHz, CDCl$_3$) δ11.5(brs, 1H), 7.11, (d, J=5.1 Hz 1H), 6.92(dd, J=5.1, 3.3 Hz, 1H), 6.81 (d, J=3.3 Hz, 1H) 5.36–5.64 (m, 4H), 4.62 (brs, 3H), 4.17–4.21 (m, 2H), 3.95–3.98 (m, 1H), 2.90–2.96 (m, 2H), 2.08–2.34 (m, 8H), 1.40–1.98(m, 6H).

Compound 4p

7-[3α,5α-Dihydroxy-2-(3α-hydroxy-5-(3-thienyl)-1E-pentenyl)cyclopentyl]-5Z-heptenoic acid According to the procedures described above for 4a, the use of dimethyl 4-(3-thienyl)-2-oxo-butylphosphonate afforded 9.6 mg of free acid 4p. While this compound is not a substituted heteroaryl derivative within the scope of general Formula I, above, it represents another aspect of this invention in view of its excellent ability to lower intraocular pressure as shown below.

$^1$H NMR (300 MHz, CDCl$_3$) δ12.0(brs, 1H), 7.23–7.27 (m, 1H), 6.94–6.95 (m, 2H), 5.36–5.65 (m, 4H), 4.10–4.17 (m, 2H), 3.94 (brs, 3H), 3.90–3.94 m, 1H), 2.68–2.74 (m, 2H), 2.00–2.35 (m, 8H), 1.44–1.96(m, 6H).

Compound 4q

7-[3α,5α-Dihydroxy-2-(3β-hydroxy-5-(3-thienyl)-1E-pentenyl)cyclopentyl]-5Z-heptenoic acid The 3β-isomer of 3p was isolated from the reaction mixture obtained in step 2 during preparation of 4p and subjected to step 3 to afford 36.2 mg of free acid 4q.

$^1$H NMR (300 MHz, CDCl$_3$) δ11.9(brs, 1H), 7.23–7.27 (m, 1H), 6.94–6.95 (m, 2H), 5.32–5.65 (m, 4H), 4.72 (brs, 3H), 4.12–4.19 (m, 2H), 3.93–3.97 (m, 1H), 2.69–2.76 (m, 2H), 2.07–2.33(m, 8H), 1.39–1.90 (m, 6H).

Compound 4r

7-[3α,5α-Dihydroxy-2-(3α-hydroxy-5-(2-(5-ethyl)thienyl-1E-pentenyl)cyclopentyl]-5Z-heptenoic acid According to the procedures described above for 4a, the use of dimethyl 4-(2-(5-ethyl)thienyl)2-oxo-butylphosphonate will result in the free acid 4r.

Compound 4s

7-[3α,5α-Dihydroxy-2-(3α-hydroxy-5-(2-(5-butyl)thienyl-1E-pentenyl)cyclopentyl]-5Z-heptenoic acid According to the procedures described above for 4a, the use of dimethyl 4-(2-(5-butyl)thienyl)2-oxo-butylphosphonate will result in the free acid 4s.

Compound 4t

7-[3α,5α-Dihydroxy-2-(3α-hydroxy-5-(2-(5-propyl)thienyl-1E-pentenyl)cyclopentyl]-5Z-heptenoic acid According to the procedures described above for 4a, the use of dimethyl 4-(2-(5-propyl)thienyl)2-oxo-butylphosphonate will result in the free acid 4t.

Compound 4u

7-[3α,5α-Dihydroxy-2-(3α-hydroxy-5-(2-(5-methoxy)thienyl-1E-pentenyl)cyclopentyl]-5Z-heptenoic acid According to the procedures described above for 4a, the use of dimethyl 4-(2-(5-methoxy)thienyl)2-oxo-butylphosphonate will result in the free acid 4u.

Compound 4v

7-[3α,5α-Dihydroxy-2-(3β-hydroxy-5-(2-thiazolyl)-1E-pentenyl)cyclopentyl]-5Z-heptenoic acid The 3β isomer of 3m was isolated from the reaction mixture obtained in Step 2 during preparation of 4m and subjected to Step 3 to afford the free acid 4v.

Compound 4w

7-[3α,5α-Dihydroxy-2-(3-hydroxy-5-(2-(3-chloro)thienyl)-1E-pentenyl)cyclopentyl]-5Z-heptenoic acid According to the process described above for 4a, the use of dimethyl 4-(2-(3-chloro) thienyl) 2-oxo-butyl phosphonate will result in the free acid 4w.

Compound 4x

7-[3α,5α-Dihydroxy-2-(3-hydroxy-5-(2-(3,4 dibromo)thienyl-1E-pentenyl)cyclopentyl]-5Z-heptenoic acid According to the procedure described above for 4a, the use of dimethyl 4-(2-(3,4 dibromo)thienyl 2-oxo-butyl phosphonate afforded the free acid 4x Compound 4y (7-[3α,5α-Dihydroxy-2-(3-hydroxy-5-(2-(5-iodo)thienyl)-1E-pentenyl)cyclopentyl]-5Z-heptenoic acid According to the procedure described above for 4a, the use of dimethyl 4-(2-(7-[3α,5α-Dihydroxy-2-(3-hydroxy-5-

(2-(5-iodo)thienyl)-1E-pentenyl)cyclopentyl]-5Z-heptenoic acid)thienyl afforded the free acid 4y Compound 4z (7-[3α,5α-Dihydroxy-2-(3-hydroxy-5-(2-(4-bromo, 5 methyl)thienyl)-1E-pentenyl)cyclopentyl]-5Z-heptenoic acid According to the procedure described above for 4a, the use of dimethyl 4-(2-(7-[3α,5α-Dihydroxy-2-(3-hydroxy-5-(2-(4-bromo, 5 methyl)thienyl)-1E-pentenyl)cyclopentyl]-5Z-heptenoic acid) thienyl afforded the free acid 4z Compound 4aa (7-[3α,5α-Dihydroxy-2-(3-hydroxy-5-(2-(3,5-dibromo)thienyl)-1E-pentenyl)cyclopentyl]-5Z-heptenoic acid According to the procedure described above for 4a, the use of dimethyl 4-(2-(7-[3α,5α-Dihydroxy-2-(3-hydroxy-5-(2-(3,5 -dibromo)thienyl)-1E-pentenyl)cyclopentyl]-5Z-heptenoic acid) thienyl afforded the free acid 4aa Compound 4ab (7-[3α,5α-Dihydroxy-2-(3-hydroxy-5-(2-(3,4 dibromo-5 methyl )thienyl)-1E-pentenyl) cyclopentyl]-5Z-heptenoic acid According to the procedure described above for 4a, the use of dimethyl 4-(2-(7-[3α,5α-Dihydroxy-2-(3-hydroxy-5-(2-(3,4 dibromo-5 methyl )thienyl)-1E-pentenyl) cyclopentyl]-5Z-heptenoic acid) thienyl afforded the free acid 4ab Compound 4ac (7-[3α,5α-Dihydroxy-2-(3-hydroxy-5-(2-(4 chloro-5 methyl)thienyl)-1E-pentenyl)cyclopentyl]-5Z-heptenoic acid According to the procedure described above for 4a, the use of dimethyl 4-(2-(7-[3α,5α-Dihydroxy-2-(3-hydroxy-5-(2-(4 chloro-5 methyl)thienyl)-1E-pentenyl)cyclopentyl]-5Z-heptenoic acid) thienyl afforded the free acid 4ac Compound 4ad (7-[3α,5α-Dihydroxy-2-(3-hydroxy-5-(2-(3 methyl )thienyl)-1E-pentenyl)cyclopentyl]-5Z-heptenoic acid According to the procedure described above for 4a, the use of dimethyl 4-(2-((7-[3α,5α-Dihydroxy-2-(3-hydroxy-5-(2-(2 methyl)thienyl)-1E-pentenyl)cyclopentyl]-5Z-heptenoic acid) thienyl afforded the free acid 4 ad Compound 6

7-[3α,5α-Dihydroxy-2-(3α-methoxy-5-(3-thienyl)-1E-pentenyl)cyclopentyl]-5Z-heptenoic acid Alcohol (400 mg, 0.694 mmol) obtained in step 2 of preparation of 4p was treated with silver triflate (803 mg, 3.12 mmol), 2,6-di-t-butyl-pyridine (0.89 mL, 3.98 mmol) and iodomethane (0.21 mL, 3.4 mmol) in $CH_2Cl_2$ (11 mL) at 0° C. After 12 h the reaction mixture was filtered through celite, concentrated in vacuo and purified by flash column chromatography to give the 3α-methoxy product 5. Further subjection of 5 to the procedures described above in step 3 of preparation of 4a provided 41.2 mg of free acid 6.

$^1$H NMR (300 MHz, $CDCl_3$) δ11.6(brs, 1H), 7.24–7.28 (m, 2H), 6.93 (d, J=3.3 Hz, 1H), 5.34–5.60 (m, 4H), 4.90 (brs, 3H), 4.20–4.23 (m, 1H), 3.99–4.02(m, 1H), 3.54–3.64 (m, 1H), 3.30 (s, 3H), 2.69 (t, J=7.3 Hz, 2H), 2.07–2.42 (m, 9H), 150–2.01 (m, 5H).

Compound 16a

7-[3α,5α-Dihydroxy-2-(3αmethoxy-5-(2-(3,4-dibromo)thienyl)-IE-pentenyl)cyclopentyl]-5Z-heptenoic acid (16a)

Methyl triflate (25 μL, 0.22 mmol) was added to a solution of 2,6-di-t-butylpyridine (60 μL, 0.27 mmol) and the corresponding alcohol prepared as above for alcohol 3a (54 mg, 0.074 mmol) in $CH_2$, $Cl_2$ (0.4 mL) at 23° C. After 12 h the reaction was diluted with $CH_2Cl_2$, and washed with 1N HCl, saturated aqueous $Na_2HCO_3$ and brine, then dried over $Na_2SO_4$, filtered and concentrated in vacuo. The residue was purified by flash column chromatography (silica gel, 3:1 hex/EtOAc) to furnish 50 mg (90%) of the methyl ester.

A solution of said methyl ester (50 mg, 0.67 mmol) and pyridinium p-toluenesulfonate (23 mg, 0.92 mmol) in MeOH (0.2 mL) was stirred at 40° C. for 12 h. After allowing the reaction to cool to room temperature the solvent was removed in vacuo. The residue was diluted with EtOAc and washed with 1N HCl, saturated aqueous $NaHCO_3$, and brine. The organic portion was then dried over $MgSO_4$, filtered and the filtrate concentrated in vacuum. Purification of the residue by flash column chromatography (silica gel, 1:1 hex/EtOAc) gave 33 mg (74%) of the 15-methoxy ester.

Lithium hydroxide (0.26 mL of a 0.5 N solution in $H_2O$, 0.13 mmol) was added to a solution of the methoxy ester (33 mg, 0.057 mmol) in THF (0.52 mL) at 23° C. After 12 h the reaction mixture was acidified with 1N HCl and extracted with EtOAc. The organic portion was washed twice with brine, dried over $Na_2SO_4$, filtered and concentrated in vacuo. The residue was purified by elution through a Sep-Pak cartridge (silica gel, 100% EtOAc followed by 9:1 $CH_2Cl_2$/MeOH) to afford 20 mg (62%) of the title compound 16a.

Compound 16b

7-[3α,5α-Dihydroxy-2-(3α-methoxy-5-(5-(3-bromo-2-methyl)thienyl)-IE-pentenyl)cyclopentyl]-5Z-heptenoic acid (16b)

In accordance with the procedures described above for the preparation of 15-methoxy acid 16a, the use of alcohol provided 25 mg of title compound 16a.

Compound 16c

7-[3α,5α-Dihydroxy-2-(3(α-methoxy-5-(2-(3,5.dibromo)thienyl)-1E-pentenyl)cyclopentyl]-5Z-heptenoic acid (16c)

In accordance with the procedures described above for the preparation of 15-methoxy acid 16a, the use of the corresponding alcohol provided 14 mg of title compound 16c.

Compound 16d

7-[3α,5α-Dihydroxy-2-(3α-methoxy-5-(5-(3,4-dibromo-2-methyl)thienyl)-1E-pentenyl) cyclopentyl]-5Z-heptenoic acid (16d)

In accordance with the procedures described above for the preparation of 15-methoxy acid 16a, the use of the corresponding alcohol provided 21 mg of title compound 16d.

Compound 16e

7-[3α,5α-Dihydroxy-2-(3α-methoxy-5-(5-(3-chloro-2-methyl)thienyl)-IE-pentenyl)cyclopentyl]-5Z-heptenoic acid (16e)

In accordance with the procedures described above for the preparation of 15-methoxy acid 16a, the use of the corresponding alcohol provided 19 mg of title compound 16e.

Compound 16f

7-[3α,5α-Dihydroxy-2-(3α-methoxy-5-(2-(3-methyl)thienyl)-IE-pentenyl)cyclopentyl]-5Z-heptenoic acid (16f)

In accordance with the procedures described above for the preparation of 15-methoxy acid 16a, the use of the corresponding alcohol provided 11 mg of title compound 16f.

Compound 16g

7-[3α,5α-Dihydroxy-2-(3α-methoxy-5-(5-(2-bromo-3-methyl)thienyl)-1E-pentenyl)cyclopentyl]-5Z-heptenoic acid (16g)

In accordance with the procedures described above for the preparation of 15-methoxy acid 16a, the use of the corresponding alcohol provided 12 mg of title compound 16 g.

Compound 8p

7-[3α,5α-Dihydroxy-2-(3α-hydroxy-5-(3-thienyl)-1E-pentenyl)cyclopentyl]-5Z-heptenamide The 3α-alcohol 3p, isolated from step 2 during preparation of 4p, was deprotected with pyridinium p-toluenesulfonate in MeOH at 45° C. for 4 h and after the usual work-up gave triol 7p.

A mixture of 7p and ammonium chloride in liquid ammonia was heated to 55° C. for 48 h in a sealed tube. The tube was recooled to −70° C., vented, and then allowed to warm to room temperature on its own accord. The residue was dissolved in 1:1 EtOAc/H$_2$O. The organic portion was separated, dried (MgSO$_4$), filtered and concentrated in vacuo. Flash column chromatography (silica gel, 9:1 CH$_2$Cl$_2$/MeOH) gave 10.9 mg of the title compound 8p.

$^1$H NMR (300 MHz, CDCl$_3$) δ7.24–7.27(m, 1H), 6.95–6.96 (m, 2H), 5.76 (brs, 1H), 5.34–5.63 (m, 4H), 4.08–4.19 (m, 2H), 3.94–3.98(m, 1H), 2.95 (brs, 3H), 2.69–2.76 (m, 2H), 2.05–2.39 (m, 8H), 1.48–1.96 (m, 6H).

Compound 8q

7-[3α,5α-Dihydroxy-2-(3β-hydroxy-5-(3-thienyl)-1E-pentenyl)cyclopentyl]-5Z-heptenamide According to the procedures described for preparation of 8p the 3β-alcohol 3g was converted to the title compound 8q.

$^1$H NMR (300 MHz, CDCl$_3$) δ7.24–7.27 (m, 1H) 6.95–6.97 (m, 2H), 5.72(brs, 2H), 5.34–5.66 (m, 4H), 4.08–4.19 (m, 2H), 3.95–3.99 (m, 1H), 3.04 (brs, 1H), 2.70–2.84 (m, 4H), 2.08–2.36 (m, 9H), 1.42–1.89 (m, 5H).

Compound 8r

7-[3α,5α-Dihydroxy-2-(3α-hydroxy-5-(3-(2,5-dichloro)thienyl)-1E-pentenyl)cyclopentyl]-5Z-heptenamide According to the procedures described for preparation of 8p the alcohol 3r was converted to the title compound 8r.

$^1$H NMR (300 MHz, CDCl$_3$) δ6.64 (s, 1H), 5.26–5.68 (m, 6H), 4.07–4.10 (m, 1H), 3.97–4.03 (m, 1H), 3.83–3.86 (m, 1H), 2.50–2.56 (m, 2H), 1.96–2.30(m, 11H), 1.39–1.80(m, 6H).

In a method analogous to the method of preparation of compounds 8p and 8q, the following compounds were prepared:

Compound 8s
7-[3α,5α-Dihydroxy-2-(3α-hydroxy-5-(3,4 dibromo) 2-thienyl)1-E pentyl)cyclopentyl]-5Z-heptenamide

Compound 8t
7-[3α,5α-Dihydroxy-2-(3α-hydroxy-5-(3-iodo)2-thienyl)1-E pentyl)cyclopentyl]-5Z-heptenamide

Compound 8u
7-[3α,5α-Dihydroxy-2-(3α-hydroxy-5-(3-methyl 4 bromo) 2-thienyl)1-E pentyl)cyclopentyl]-5Z-heptenamide

Compound 8v
7-[3α,5α-Dihydroxy-2-(3α-hydroxy-5-(3,4 dibromo )2-thienyl)1-E pentyl)cyclopentyl]-5Z-heptenamide

Compound 8w
7-[3α,5α-Dihydroxy-2-(3α-hydroxy-5-(3-methyl, 4, 5 dibromo)-2-thienyl)1-E pentyl)cyclopentyl]-5Z-heptenamide

Compound 8x
7-[3α,5α-Dihydroxy-2-(3α-hydroxy-5-(3-methyl, 4 chloro)-2-thienyl)1-E pentyl)cyclopentyl]-5Z-heptenamide

Compound 8y
7-[3α,5α-Dihydroxy-2-(3α-hydroxy-5-(5-methyl 2-thienyl)1-E pentyl)cyclopentyl]-5Z-heptenamide

Compound 8z
7-[3α,5α-Dihydroxy-2-(3α-hydroxy-5-(2-(3-methyl) thienyl)-IE-pentenyl)cyclopentyl]-5Z-heptenamide 8z

Compound 8aa
7-[3α,5α-Dihydroxy-2-(3α-hydroxy-5-(5-(2-iodo) thienyl)-IE-pentenyl)cyclopentyl]-5Z-heptenamide (8aa)

Compound 8ab
7-[3α,5α-Dihydroxy-2(3α-hydroxy-5-(5-(3-bromo-2-methyl)thienyl)-IE-pentenyl)cyclopentyl]-5Z-heptenamide (8ab)

Compound 8ac
7-[3α,5α-Dihydroxy-2-(3α-hydroxy-5-(2-(3,5-dibromo)tbienyl)-I-pentenyl)-cyclopentyl]-5Z-heptenamide (8ac)

Compound 8ad
7-[3α,5α-Dihydroxy-2-(3α-hydroxy-5-(5-(3,4-dibromo-2-methyl)-thienyl)-1E-pentenyl) cyclopentyl]-5Z-heptenamide (8ad)

Compound 8ae
7-[3α,5α-Dihydroxy-2-(3α-hydroxy-5-(5-(3-chloro-2-methyl)thienyl)-IE-pentenyl)cyclopentyl]-5Z-heptenamide (8ae)

Compound 8af
7-[3α,5α-Dihydroxy-2-(3α-hydroxy-5-(2-(3-methyl) thienyl)-IE-pentenyl)cyclopentyl]-5Z-heptenamide (8af)

Compound 13
7-[3α,5α-Dihydroxy-2-(3α-hydroxy-5-(3-thienyl) pentyl)cyclopentyl]-5Z-heptenoic acid Step 1:Preparation of Alcohol To a suspension of sodium hydride 271 mg (11.30 mmol) in THF (21 mL) cooled to 0° C. was added a solution of dimethyl 4-(3-thienyl)-2-oxo-butylphosphonate (2.96g, 11.30 mmol) in THF (10 mL). After stirring for 0.5 h a solution of aldehyde 9 (2.80 g, 10.28 mmol) in THF (10 mL) was added dropwise. The reaction was allowed to warm to room temperature and stirred for a total of 12 h before quenching with saturated aqueous $NH_4Cl$. The mixture was extracted with EtOAc and the organic portion was washed with saturated aqueous $NaHCO_3$, brine, dried ($MgSO_4$), filtered and concentrated in vacuo. The residue was purified by flash column chromatography (silica gel, 1:1 hex/EtoAc) to afford 3.98, (95%) of enone.

Immediately, a solution of the enone (3.98 g, 9.75 mmol) in MeOH (22 mL) was cooled to 0° C. and sodium tetrahydridoborate (369 mg, 9.75 mmol) was added. After 2 h the reaction was quenched with saturated aqueous $NH_4Cl$ and extracted with EtOAc. The organic portion was washed with brine, dried ($MgSO_4$) filtered and concentrated in vacuo. Purification by HPLC (Waters Partisil-10, 1:1 hex/EtOAc) afforded 1.30 g (33%) of the α-alcohol 10.

$^1H$ NMR (300 MHz, $CDCl_3$) δ7.97 (d, J=7.2 Hz, 2H), 7.21–7.57, (m, 4H), 6.88 (d, J=4.1 Hz, 2H), 5.54–5.70 (m, 2H), 5.23 (q, J=6.1 Hz, 1H), 5.04 (t, J=6.5 Hz, 1H), 4.10 (q, J=7.1 Hz 1H), 2.45–2.89 (m, 7H), 2.18–2.26 (m, 2H), 1.76–184 (m, 2H).

Step 2: Preparation of Bis-Silyl ether 11

Potassium carbonate (523 mg, 3.78 mmol) was added to a solution of benzoate 10 (1.3 g, 3.15 mmol) in MeOH(6.5 mL). After 16 h the reaction solvent was removed in vacuo and the residue was dissolved in EtOAc/saturated aqueous $NH_4Cl$. The organic portion was washed with brine, dried ($MgSO_4$), filtered and concentrated in vacuo.

The residue was dissolved in THF (6.5 mL) and triphenylphosphine rhodium chloride (400 mg) was added. The solution was degassed and purged under an atmosphere of hydrogen gas at 40–45 psi. After 16 h the reaction was concentrated in vacuo, and the residue purified by flash column chromatography (silica gel, 3:1 hex/EtOAc) to afford the apparent saturated diol after evaporation of the solvents.

The apparent diol was dissolved in $CH_2Cl_2$ (6.5 mL) and 2,6-lutidine (2.0 mL, 16.5 mmol) was added followed by t-butyldimethylsilyl triflate (3.0 mL, 13.2 mmol). The reaction was quenched with saturated aqueous $NaHCO_3$ and washed with brine, dried ($MgSO_4$), filtered and concentrated in vacuo. Flash column chromatography (9:1 hex/EtOAc) gave 1.29 g (94%) of the bis-TBDMS ether 11.

$^1H$ NMR (300 MHz, $CDCl_3$) δ7.22–7.25 (m, 1H), 7.22–7.23 (m, 2H), 4.92–4.98 (m, 1H), 3.90–3.94 (m, 1H), 3.64–3.70 (m, 1H), 2.45–2.82 (m, 5H), 1.95–2.16 (m, 2H), 1.71–1.77 (m, 3H), 1.05–1.51 (m, 4H), 0.88 (s, 9H), 0.85 (s, 9H), 0.03 (s, 9H), 0.02 (s, 3H).

Step 3: Preparation of ester 12

Lactone 11 (170 mg, 0.315 mmol) was dissolved in $CH_2Cl_2$ (1.0 mL) and cooled to −70° C. Dibal-H(0.47 mL of a 1.0 M solution in $CH_2Cl_2$, 0.47 mmol) was added. After 2 h the reaction was quenched with MeOH, allowed to warm to room temperature, and extracted with $CH_2Cl_2$. The organic portion was dried ($Na_2SO_4$), filtered and concentrated in vacuo to give the lactol as a clear, viscous oil.

To a suspension of (4-carboxybutyl) triphenylphosphonium bromide (558 mg, 1.26 mmol) in THF (2.5 mL) was added potassium bis (trimethylsilyl) amide(503 mg, 2.52 mmol) at 0° C. After 0.5 h the solution was cooled to −70° C. and a solution of the lactol in THF (2.5 mL) was added. The reaction was allowed to warm to room temperature on its own accord, quenched with saturated aqueous $NH_4Cl$, and extracted with EtOAc. The organic portion was washed with saturated aqueous $NaHCO_3$, brine, dried ($MgSO_4$), filtered and concentrated in vacuo. The residue was diluted with $Et_2O$ and excess diazomethane in $Et_2O$ was added until the reaction solution persisted yellow. Evaporation of the solvent gave 140 mg (70%) of ester 12.

$^1H$ NMR (300 MHz, $CDCl_3$) δ7.22–7.24 (m, 1H), 6.90–6.92 (m, 2H), 5.28–5.52 (m, 2H), 4.02–4.06 (m, 1H), 3.95–3.96 (m, 1H), 3.63–3.67 (m, 1H), 3.63 (s, 3H), 2.52–2.70 (m, 2H), 2.00–2.32 (m, 5H), 1.20–1.84 (m, 14H), 0.88 (s, 9H), 0.86 (s, 9H), 0.108–0.055 (m, 12H), (d, J=7.2 Hz, 2H), 7.21–7.57, (m, 4H), 6.88 (d, J=4.1 Hz, 2H), 5.54–5.70 (m, 2H), 5.23 (q, J=6.1 Hz, 1H), 5.04 (+, J=6.5 Hz, 1H), 4.10 (q, J−7.1 Hz 1H), 2.45–2.89 (m, 7H), 2.18–2.26 (m, 2H), 1.76–1.84 (m, 2H).

Step 4: Preparation carboxylic acid 13

To a solution of bis-TBDMS ether 12 (25 mg, 0.040 mmol) in THF (0.24 mL) was added $Bu_4NF$ (0.12 mL of a 1.0M solution in THF, 0.12 mmol). After 16 h the reaction was concentrated in vacuo and purified by flash column chromatography (silica gel, 3:1 hex/EtOAc) to yield 13.0 mg (79%) of the triol.

Lithium hydroxide (0.15 mL of a 0.5N solution in $H_2O$ 0.073 mmol) was added to a solution of the ester (13.0 mg, 0.0316 mmol) in THF (0.3 mL). After 16 h the reaction was acidified with 1N HCl and extracted with EtOAc. The organic portion was dried ($MgSO_4$), filtered and concentrated in vacuo to give 7.0 mg (56%) of free acid 13.

$^1H$ NMR (300 MHz, $CDCl_3$) δ12.0 (brs, 1H), 7.19–7.22 (m, 1H), 6.90–6.92 (m, 2H), 5.31–5.48 (m, 2H), 4.10 (+, J=3.9 Hz, 1H), 3.86–3.88 (m, 1H), 3.59–3.65 (m, 1H), 2.65–2.82 (m, 2H), 1.20–2.30 (m, 21H).

Compound 15

7-[3α,5α-Dihydroxy-2-(3-hydroxy-5-(3-furanyl) pentyl) cyclopentyl]-5Z-heptenoic acid 15

Step 1: Preparation of ketone 14

A mixture of the enone (137 mg, 0.245 mmol) obtained in step 2 of preparation of 4k above, Aliquat 336 (34 μL, 0.074 mmol), sodium dithionite (384.7 mg, 2.21 mmol) and sodium bicarbonate (371.3 mg, 4.42 mmol) in benzene: $H_2O$ (1:1, 6.0 mL) was heated to 75° C. for 1.5 h. The reaction mixture was allowed to cool to room temperature, was diluted with EtoAc, and was washed with $H_2O$ and brine. The organic portion was dried ($MgSO_4$), filtered and the filtrate was concentrated in vacuo. Purification by flash column chromatography (silica gel, 4:1 hex/EtOAc) gave 113.3 mg (83%) of the ketone 14.

Step 2: Preparation of 7-[3α,5α-Dihydroxy-2-(3-hydroxy-5-(3-furanyl)pentyl)cyclopentyl]-5Z-heptenoic acid 15

Sodium tetrahydridoborate (14.2 mg, 0.375 mmol) was added to a solution of the ketone (210 mg, 0.375 mmol) in MeOH (3.0 mL) cooled to 0° C. After 30 minutes the reaction was quenched with saturated aqueous ammonium chloride and allowed to warm to room temperature. The mixture was extracted with $Et_2O$ and the organic portion was dried ($MgSO_4$), filtered and concentrated in vacuo.

The residue was diluted with MeOH (3.0 mL) and pyridinium p-toluene sulfonate (141 mg, 0.562 mmol) was added. After heating to 45° C. for 16 h the reaction was concentrated in vacuo, diluted with EtOAc and washed with 1 N HCl, saturated aqueous sodium bicarbonate, brine, dried (MgSO$_4$), filtered and concentrated in vacuo. Flash column chromatography (silica gel, 2:1 hex/EtOAc) followed by 100% EtOAc) gave 123 mg (83%) of a mixture of alcohols which were homogenous by TLC.

The mixture of alcohols (52.3 mg, 0.132 mmol) was diluted with THF (1.0 mL) and lithium hydroxide (0.53 mL of a 0.5 N solution in H$_2$O, 0.265 mmol) was added. After 16 h the reaction was acidified with 1 N HCl and extracted with EtOAc. The organic portion was washed with brine, dried (MgSO$_4$) filtered and concentrated in vacuo to afford 44.6 mg (89%) of free acid 15.

$^1$H NMR (300 MHz, CDCl$_3$) δ7.34 (d, J=1.8 Hz, 1H), 7.23 (s, 1H), 6.2 (d, J=1.8 Hz, 1H), 5.30–5.52 (m, 2H), 4.81 (brs, 3H) 4.16 (brs, 1H), 3.95 (brs, 1H), 3.61–3.72 (m, 1H), 2.10–2.64 (m, 7H), 2.17 (s, 3H), 1.34–1.91 (m, 10H).

Compound 16a

Isopropyl 7-[3α,5α-Dihydroxy-2-(3α-hydroxy-5-(2-(3-methyl)thienyl)-IE-pentenyl)cyclopentyl]-5Z-heptenoate (16a)

A solution of free acid 5g (17.5 mg, 0.043 mmol), 2-iodopropane (21 μL, 0.22 mmol) and 1,8-diazabicyclo[5.4.0]undec-7-ene (20 μL, 0.13 mmol) in acetone (0.1 mL) was stirred at 23° C. for 12 h. The reaction mixture was concentrated in vacuo and the residue was purified by flash column chromatography (silica gel, 3:1 EtOAc/hexane) to yield 15 mg (77%) of the isopropyl ester 10 g.

By analoguous methods of synthesis, the following compounds of the invention are prepared:

Compound 17a
7-[3α,5α-Dihydroxy-2-(3α-hydroxy-5-(2-(5-cyano)thienyl)-1E-pentenyl)cyclopentyl]-5Z-heptenoic acid Compound 17b
7-[3α,5α-Dihydroxy-2-(3α-hydroxy-5-(2-(5-cyano)thienyl)-1E-pentenyl)cyclopentyl]-5Z-heptenamide Compound 17c
Isopropyl-7-[3α,5α-Dihydroxy-2-(3α-hydroxy-5-(2-(5-cyano)thienyl)-1-E-pentenyl)cyclopentyl]-5Z-heptenoate Compound 18a
7-[3α,5α-Dihydroxy-2-(3α-hydroxy-5-(2-(3-fluoro)thienyl)-1-E-pentenyl)cyclopentyl]-5Z-heptenoic acid Compound 18b
7-[3α,5α-Dihydroxy-2-(3α-hydroxy-5-(2-(3-fluoro)thienyl)-1-E-pentenyl)cyclopentyl]-5Z-heptenamide Compound 19a
N-Methylsulfonyl-7-[3α,5α-Dihydroxy-2-(3α-hydroxy-5-(3-(2-methyl)thienyl)-1E-pentenyl)cyclopentyl]-5Z-heptenamide Compound 19b
N-Ethylsulfonyl-7-[3α,5α-Dihydroxy-2-(3α-hydroxy-5-(3-(2-methyl)thienyl)-1E-pentenyl)cyclopentyl]-5Z-heptenamide Compound 19c
N-Trifluoromethylsulfonyl-7-[3α,5α-Dihydroxy-2-(3α-hydroxy-5-(3-(2-methyl)thienyl)-1E-pentenyl)cyclopentyl]-5Z-heptenamide Compound 20a
N-Methylsulfonyl-7-[3α,5α-Dihydroxy-2-(3α-hydroxy-5-(2-(5-chloro)thienyl)-1E-pentenyl)cyclopentyl]-5Z-heptenamide Compound 20b
N-Ethylsulfonyl-7-[3α,5α-Dihydroxy-2-(3α-hydroxy-5-(2-(5-chloro)thienyl)-1E-pentenyl)cyclopentyl]-5Z-heptenamide Compound 20c
N-Trifluoromethylsulfonyl-7-[3α,5α-Dihydroxy-2-(3α-hydroxy-5-(2-(5-chloro)thienyl)-1E-pentenyl)cyclopentyl]-5Z-heptenamide Compound 21a
N-Methylsulfonyl-7-[3α,5α-Dihydroxy-2-(3α-hydroxy-5-(2-(5-iodo)thienyl)-1E-pentenyl)cyclopentyl]-5Z-heptenamide Compound 21b
N-Ethylsulfonyl-7-[3α,5α-Dihydroxy-2-(3α-hydroxy-5-(2-(5-iodo)thienyl)-1E-pentenyl)cyclopentyl]-5Z-heptenamide Compound 21c
N-Trifluoromethylsulfonyl-7-[3α,5α-Dihydroxy-2-(3α-hydroxy-5-(2-(5-iodo)thienyl)-1E-pentenyl)cyclopentyl]-5Z-heptenamide Compound 22a
N-Methylsulfonyl-7-[3α,5α-Dihydroxy-2-(3α-hydroxy-5-(3-(2-methyl)thienyl)-1E-pentenyl)cyclopentyl]-5Z-heptenamide Compound 22b
N-Ethylsulfonyl-7-[3α,5α-Dihydroxy-2-(3α-hydroxy-5-(3-(2-methyl)thienyl)-1E-pentenyl)cyclopentyl]-5Z-heptenamide Compound 22c
N-Trifluoromethylsulfonyl-7-[3α,5α-Dihydroxy-2-(3α-hydroxy-5-(3-(2-methyl)thienyl)-1E-pentenyl)cyclopentyl]-5Z-heptenamide Compound 23a
N-Methylsulfonyl-7-[3α,5α-Dihydroxy-2-(3α-hydroxy-5-(2-(5-bromo)thienyl)-1E-pentenyl)cyclopentyl]-5Z-heptenamide Compound 23b
N-Ethylsulfonyl-7-[3α,5α-Dihydroxy-2-(3α-hydroxy-5-(2-(5-bromo)thienyl)-1E-pentenyl)cyclopentyl]-5Z-heptenamide Compound 23c
N-Trifluoromethylsulfonyl-7-[3α,5α-Dihydroxy-2-(3α-hydroxy-5-(2-(5-bromo)thienyl)-1E-pentenyl)cyclopentyl]-5Z-heptenamide Compound 24
N-Methylsulfonyl-N-acetylmethyl-7-[3α,5α-Dihydroxy-2-(3α-hydroxy-5-(2-(5-bromo)thienyl)-1E-pentenyl)cyclopentyl]-5Z-heptenamide Compound 25
N-Methylsulfonyl-N-pivaloylmethyl-7-[3α,5α-Dihydroxy-2-(3α-hydroxy-5-(2-(5-bromo)thienyl)-1E-pentenyl)cyclopentyl]-5Z-heptenamide Certain of the sulfonyl compounds, above, may be synthesized according to the procedures disclosed in U.S. patent application Ser. No. 09/880,272 filed on Jun. 13, 2001 in the names of David W. Old and Robert M. Burk, which is hereby incorporated by reference in its entirety.

Certain of the above compounds were tested for activity in the various in vitro assays described below and the results are reported in Tables below.

Activity at different prostanoid receptors was measured in vitro in isolated smooth muscle preparations. FP-activity was measured as contraction of the isolated feline iris sphincter. $EP_1$-activity was measured as contraction of the longitudinal smooth muscle of the isolated guinea pig ileum. $EP_3$-activity was measured as inhibition of the twitch response induced by electrical field stimulation in the isolated guinea pig was deferens and as contraction of the longitudinal smooth muscle of the isolated chick ileum. Activity was also measured as relaxation of smooth muscle of isolated rabbit jugular vein a preparation which appears to contain a unique $PGF_{2\alpha}$-sensitive receptor provisionally termed $FP_{VASC}$. TP-vasoconstrictor activity was measured as contraction of rings of the isolated rat thoracic aorta. Effects on platelets from healthy human donors were measured by incubating platelet-rich plasma with the compounds described herein. Inhibition of aggregation was determined by the ability of the compounds described herein to inhibit platelet aggregation in platelet-rich plasma induced by 20 $\mu$M ADP.

In addition to stimulating the FP receptor associated with the cat iris, several examples also stimulated the $EP_3$ receptor. Compounds with agonist activity at $EP_3$ receptors may also be used for treating gastric or duodenal ulcer by virtue of their cytoprotective and anti-secretory properties. They may also be used as adjunctive therapy in combination with aspirin-like drugs and steroids to limit gastrointestinal side effects. $EP_3$ agonists stimulate uterine smooth muscle and may be used to terminate pregnancy in human females. $EP_3$ agonists are also useful in the cervical ripening process and could be used for inducing labor.

Other potential therapeutic applications are in osteoporosis, constipation, renal disorders, sexual dysfunction, baldness, diabetes, cancer and in disorder of immune regulation.

Many examples also have pronounced activity at the FP receptor, provisionally termed $FP_{VASC}$ associated with the vascular endothelium in the rabbit jugular vein preparation. Since such agents would be vasodilators they have potential in hypertension and any disease where tissue blood perfusion is compromised. Such indications include, but are not limited to, systemic hypertension, angina, stroke, retinal vascular diseases, claudication, Raynauds disease, diabetes, and pulmonary hypertension.

The effects of the compounds of this invention on intraocular pressure are also provided in the following tables. The compounds were prepared at the said concentrations in a vehicle comprising 0.1% polysorbate 80 and 10 mM TRIS base. Dogs were treated by administering 25 $\mu$l to the ocular surface, the contralateral eye received vehicle as a control. Intraocular pressure was measured by applanation pneumatonometry. Dog intraocular pressure was measured immediately before drug administration and at 6 hours thereafter.

Compounds 4g, 8t, 8u, 8v and 6g were examined and showed a pronounced ocular hypotensive effect in dogs.

| AGN-# | FP | EP$_1$ | EP$_3$ | FP$_{VASC}$ | TP | Platelets aggreg | inhib | Dog IOP (1 day) | Hyp/ Miosis |
|---|---|---|---|---|---|---|---|---|---|
| 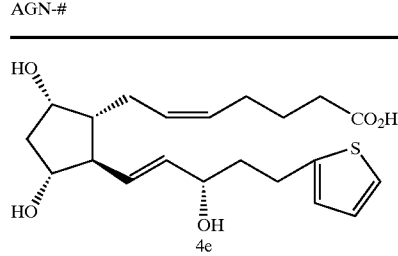 4e | 4.2 | >10$^4$ | 43 p.a. 1230 | 20 | 4010 | NA | NA | 0.1%/−2.8 | 0.38/pinpt |
| 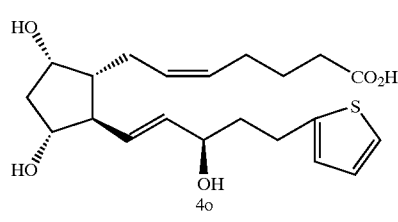 4o | 82 | >10$^4$ | >10$^4$ 1820 | 31 | >10$^4$ | | | 0.1%/−4.2 | 0.79/pinpt |
| 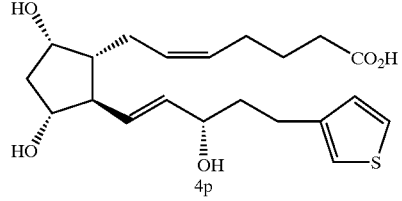 4p | 0.8 | 2000 | 400 178 | 9.2 | 2460 | NA | NA | 0.1%/−6.0 | 0.6/pinpoint |

-continued

| AGN-# | FP | EP₁ | EP₃ | FP$_{VASC}$ | TP | Platelets aggreg | inhib | Dog IOP (1 day) | Hyp/ Miosis |
|---|---|---|---|---|---|---|---|---|---|
| 8p | 3.5 | >10⁴ | >10⁴ / 5000 | 3.6 | >10⁴ | | | | |
| 4q | 30 | | 58 | | | | | | |
| 8q | 170 | | | | | | | 0.1%/−3.3 | 0.72*/pin |
| 6 | 0.8 | >10⁴ pa | 189 pa / 1060 | 2.1 | ~10⁴ | NA | NA | 0.1%/−2.1 | 0.83/pinpt |
| 13 | 10 | >10⁴ | 105 pa / 2400 | 545 | 4740 | NA | NA | | |
| 4k | 19 | >10⁴ | 83 / 2510 | | 5400 | | | 0.1%/−3.6 / 0.01%/−2.5 | 0.38/pinpoint / 0.83/mild |
| 15 | 137 | | >5882 | | | | | | |

-continued

| AGN-# | FP | EC₅₀ (nM) EP₁ | EP₃ | FP_VASC | TP | Platelets aggreg | inhib | Dog IOP (1 day) | Hyp/Miosis |
|---|---|---|---|---|---|---|---|---|---|
| 4l | 9 | >10$^4$ | 44<br>1150 | >7692 | ~10$^4$ | | | 0.1%/−4.3<br>0.01%/−1.7 | 0.67/pinpoint<br>0.54/mild |
| 4a | 12 | >10$^4$ | 355<br>3470 | >833 | 3980 | | | | |
| 4j | 190 | | 9000 pa | >68966 | | | | 0.1%/0<br>0.01%/−1.2 | 0.13/0<br>0.17/0 |
| 4i | 291 | | ~10$^4$ | 2664 | | | | | |
| 4d | 4 | >10$^4$ | 1000 pa<br>6170 | 47 | 2450 | | | 0.1%/−3.3 | 1.13/pinpoint |
| 4b | 7 | >10$^4$ | 341 pa<br>8710 | >7692 | >10$^4$ | | | | |

-continued

| AGN-# | FP | EC₅₀ (nM) EP₁ | EP₃ | FP$_{VASC}$ | TP | Platelets aggreg | inhib | Dog IOP (1 day) | Hyp/ Miosis |
|---|---|---|---|---|---|---|---|---|---|
| 4c | 3 | >10⁴ | 305 pa 2040 | >7143 | ~10⁴ | | | 0.1%/−4.5 0.01%/−2.9 | 1.38/pinpt 0.42/pinpt |
| 4e | 0.8 | >10⁴ | 50 pa 2190 | 16 | 371 | | | | |
| 4g | 0.49 | >10⁴ | >10⁴ pa >10⁴ | 7.7 | 2300 | | | 0.1%/−5.6 | 0.5/pinpt |
| 4f | 4 | >10⁴ | 36 pa 7410 | 8.5 | 5080 | | | 0.1%/−4.8 | 1.0/pinpoint |
| 4m | 503 | | 1003 | | | | | 0.1%/−3.2 | 0.6/pinpoint |
| 4v | 4230 | | 28325 | | | | | | |

-continued
| AGN-# | FP | EC$_{50}$ (nM) EP$_1$ | EP$_3$ | FP$_{VASC}$ | TP | Platelets aggreg | inhib | Dog IOP (1 day) | Hyp/ Miosis |
|---|---|---|---|---|---|---|---|---|---|
| 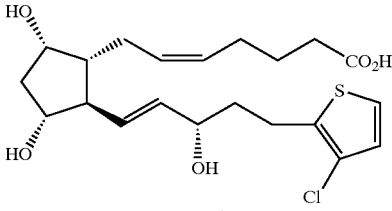 4h | 13 | >10$^4$ >10$^4$ | = 10$^4$ pa | 122 | 3530 | | | | |
| 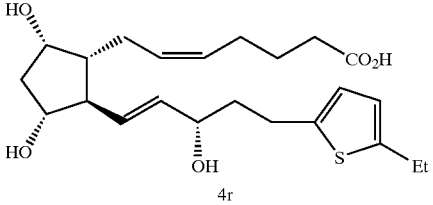 4r | 33 | | 21 | | >10$^4$ | | | | |
| 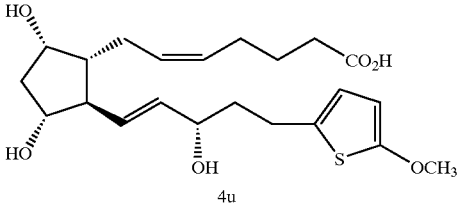 4u | 202 | | | | | | | | |
| 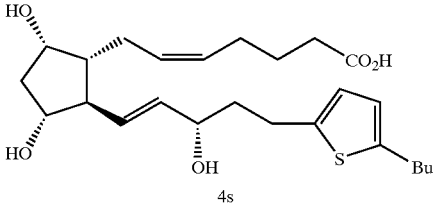 4s | 2940 | | | | | | | | |
| 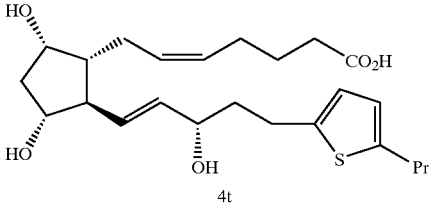 4t | 53 | | | | | | | | |
| 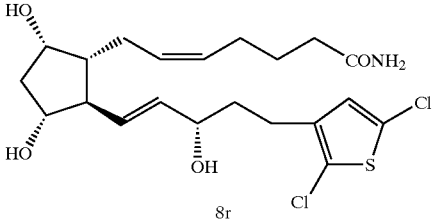 8r | 0.70NA | | | 82 | >10$^4$ | | | 0.1%/−5.8 | 1.2/pinpoint |

| Compound # | Structure | feFP/ OHL | rbFP$_v$/ EP$_4$ | rtTP$_{va}$ | hTP$_{pl}$ | hFP (Ca) | hEP$_1$ (Ca) | hTP (Ca) |
|---|---|---|---|---|---|---|---|---|
| 17a | 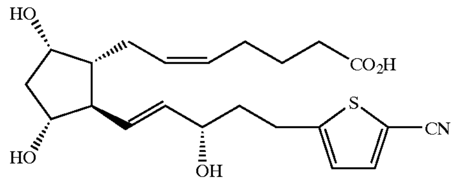 | 43 | 112 | ~$10^4$ | | | >$10^4$ | |
| 17b | 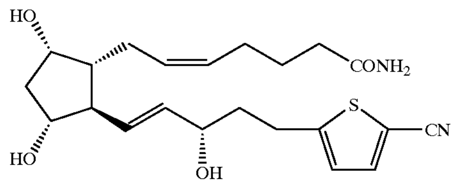 | 2950 | >256,400 | | | | | |
| 17c | 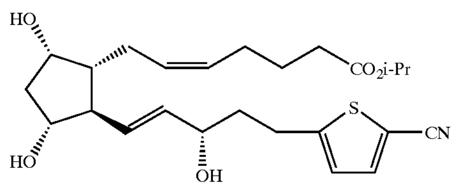 | 115 | 6,510 | | | | | |
| 18a | 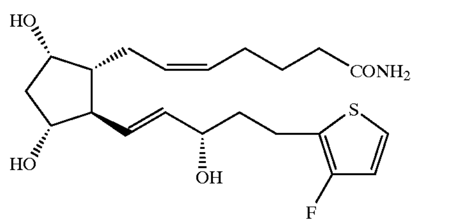 | 7.0 | 537 | NA | | | NA | |
| 18b | 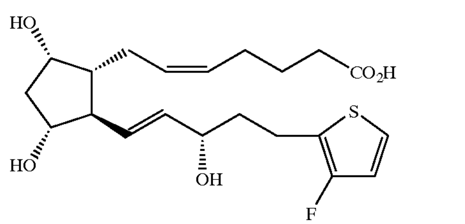 | 3.2 | 2.9 | 3498 | | | >$10^4$ pa | |
| 19a | 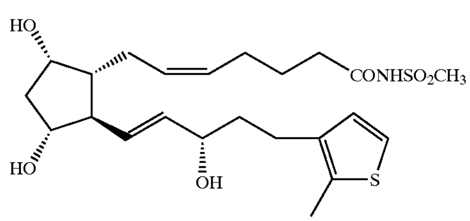 | 13 | | | | | | |
| 19b | 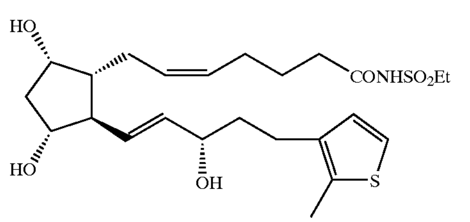 | 23 | | | | | | |

-continued

| Compound # | Structure | feFP/ OHL | rbFP$_v$/ EP$_4$ | rtTP$_{va}$ | hTP$_{pl}$ | hFP (Ca) | hEP$_1$ (Ca) | hTP (Ca) |
|---|---|---|---|---|---|---|---|---|
| 19c | (structure with 2-methylthiophene, CONHSO$_2$CF$_3$) | 50 | | | | | | |
| 20a | (structure with 5-chlorothiophene, CONHSO$_2$CH$_3$) | 7.9 | 6073 | NA | | | | |
| 20b | (structure with 5-chlorothiophene, CONHSO$_2$Et) | 5.5 | 1036 | | | | | |
| 20c | (structure with 5-chlorothiophene, CONHSO$_2$CF$_3$) | 4.2 | 221 | >>10$^4$ | | | | |
| 21a | (structure with 5-iodothiophene, CONHSO$_2$CH$_3$) | 5.6 | 1821 | | | | | |
| 21b | (structure with 5-iodothiophene, CONHSO$_2$Et) | 6.8 | 189 | | | | | |
| 21c | (structure with 5-iodothiophene, CONHSO$_2$CF$_3$) | 5.5 | 36 | | | | | |

-continued

| Compound # | Structure | feFP/ OHL | rbFP$_v$/ EP$_4$ | rtTP$_{va}$ | hTP$_{pl}$ | hFP (Ca) | hEP$_1$ (Ca) | hTP (Ca) |
|---|---|---|---|---|---|---|---|---|
| 22a | *structure with CONHSO$_2$CH$_3$ and 2-methylthiophene* | 169 | 22586 | | | | | |
| 22b | *structure with CONHSO$_2$Et and 2-methylthiophene* | 424 | | | | | | |
| 22c | *structure with CONHSO$_2$CF$_3$ and 2-methylthiophene* | 291 | | | | | | |
| 23a | *structure with CONHSO$_2$CH$_3$ and 5-bromothiophene* | 5.0 | | | | 387 | >10$^4$ | |
| 23b | *structure with CONHSO$_2$Et and 5-bromothiophene* | 3.4 | | | | 108 | 117 | |
| 23c | *structure with CONHSO$_2$CF$_3$ and 5-bromothiophene* | 9.2 | | | | 12 | 6.0 | |
| 24 | *structure with N(CH$_2$OAc)(SO$_2$CH$_3$) amide and 5-bromothiophene* | 4.0 | | | | 45 | 26 | |

-continued

| Compound # | Structure | feFP/ OHL | rbFPv/ EP4 | rtTPva | hTPpl | hFP (Ca) | hEP1 (Ca) | hTP (Ca) |
|---|---|---|---|---|---|---|---|---|
| 25 | 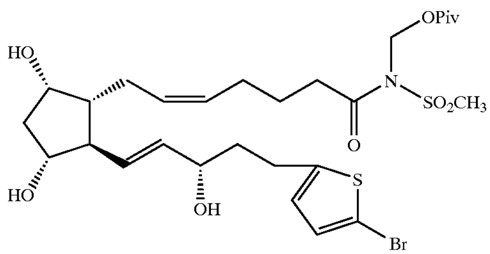 | 4.9 | | | | | 65 | 64 |

The compounds of the invention may also be useful in the treatment of various pathophysiological diseases including acute myocardial infarction, vascular thrombosis, hypertension, pulmonary hypertension, ischemic heart disease, congestive heat failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petroatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules make of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tables or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension which administering to a mammal having ocular hypertension a therapeutically-effective amount of a compound wherein said compound is represented by formula II:

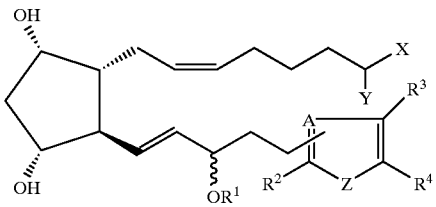

wherein the hatched segments represent a bonds, the solid triangle represents a b bond, wavy line attachments indicate either the alpha (a) or beta (b) configuration;

$R^1$ is hydrogen or a lower alkyl radical having up to six carbon atoms, X is selected from the group consisting of $OR^1$, $-N(R1)2$, and $-N(R^5)SO_2R^6$, wherein $R^5$ represents hydrogen or $CH_2OR^6$ and $R^6$ represents hydrogen or a lower alkyl radical having up to six carbon atoms and halogen substituted derivatives of said lower alkyl radical;

Y is $=O$ or represents 2 hydrogen radicals, Z is selected from the group consisting of O and S, A is selected from the group consisting of N, $-CH$, and C, $R^2$ is selected from the group consisting of hydrogen, halogen and lower alkyl having from 1 to 6 carbon atoms, $R^3$ and $R^4$ are selected from the group consisting of hydrogen, halogen, lower alkyl having from 1 to 6 atoms, or, together with,

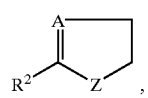

$R^3$ and $R^4$ forms a condensed aryl ring;

provided however when A is selected from the group consisting of CH and C, $R^3$ and $R^4$ together with

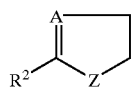

forms a condensed aryl ring.

2. The method of claim 1 wherein said compound represented by formula IV:

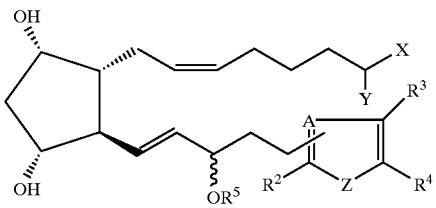

wherein $R^5$ is hydrogen or methyl.

3. The method of claim 2 wherein Z is S.

4. The method of claim 3 wherein at least one of $R^2$, $R^3$ and $R^4$ are selected from the group consisting of halogen and lower alkyl having from 1 to 4 carbon atoms.

5. The method of claim 3 wherein at least one of $R^2$, $R^3$ and $R^4$ is selected from the group consisting of chloro, bromo and iodo.

6. The method of claim 3 wherein at least one of $R^2$, $R^3$ and $R^4$ are bromo.

7. The method of claim 3 wherein $R^5$ is selected from the group consisting of hydrogen,

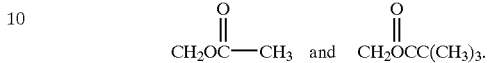

8. The method of claim 3 wherein $R^6$ is selected from the group consisting of methyl, ethyl and trifluoromethyl.

9. A pharmaceutical product, comprising a container adapted to dispense the contents of said container in metered form; and an ophthalmic solution in said container comprising a compound of formula II as defined in claim 1, or a pharmaceutically acceptable salt thereof, in admixture with a non-toxic, ophthalmically acceptable liquid vehicle.

10. The compound is represented by Formula III:

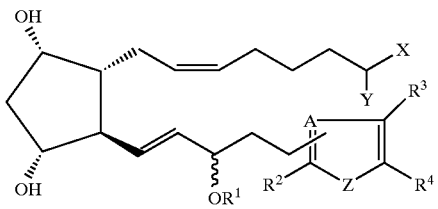

wherein $R^1$ is hydrogen or a lower alkyl radical having up to six carbon atoms, X is selected from the group consisting of $-OR^1$, $-N(R^1)_2$, and $-N(R^5)SO_2R^6$, wherein $R^5$ represents hydrogen or $CH_2OR^6$ and $R^6$ represents hydrogen or a lower alkyl radical having up to six carbon atoms and halogen substituted derivatives of said lower alkyl radical;

Y is $=O$ or represents 2 hydrogen radicals;

Z is selected from the group consisting of O and S, A is selected from the group consisting of N, $-CH$, and C, $R^2$ is selected from the group consisting of hydrogen, halogen and lower alkyl having from 1 to 6 carbon atoms, $R^3$ and $R^4$ are selected from the group consisting of hydrogen, halogen, lower alkyl having from 1 to 6 carbon atoms, or, together with

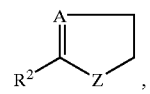

$R^3$ and $R^4$ forms a condensed aryl ring;

provided however when A is selected from the group consisting of CH and C, $R^3$ and $R^4$ together with

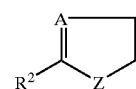

with forms a condensed aryl ring.

11. The compound of claim 10 wherein said compound is represented by formula IV:

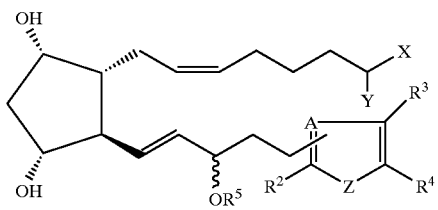

wherein $R^5$ is hydrogen or methyl.

12. The compound of claim 11 wherein Z is S.

13. The compound of claim 12 wherein at least one of $R^2$, $R^3$ and $R^4$ are selected from the group consisting of halogen and lower alkyl having from 1 to 4 carbon atoms.

14. The compound of claim 12 wherein at least one of $R^2$, $R^3$ and $R^4$ is selected from the group consisting of chloro, bromo and iodo.

15. The compound of claim 12 wherein at least one of $R^2$, $R^3$ and $R^4$ are bromo.

16. The compound of claim 12 wherein $R^5$ is selected from the group consisting of hydrogen,

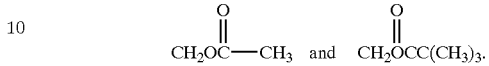

17. The compound of claim 12 wherein $R^6$ is selected from the group consisting of methyl, ethyl and trifluoromethyl.

* * * * *

UNITED STATES PATENT AND TRADEMARK OFFICE
CERTIFICATE OF CORRECTION

PATENT NO.    : 6,602,900 B2
DATED         : August 5, 2003
INVENTOR(S)   : Robert M. Burk It is certified that error appears in the above-identified patent and that said Letters Patent is hereby corrected as shown below:

Column 9,
Line 10, delete "393" and insert in place thereof -- 3.93 --

Column 10,
Line 20, delete "1-E" and insert in place thereof -- 1E --

Column 11,
Line 15, delete "122" and insert in place thereof -- 1.22 --

Column 14,
Line 7, delete "150" and insert in place thereof -- 1.50 --

Column 16,
Line 48, delete "I" and insert in place thereof -- IE --

Column 19,
Lines 38, 41 and 45, delete "I-E" and insert in place thereof -- IE --

Column 39,
Line 21, delete "OR$^1$" and insert in place thereof -- OR$_1$ --
Lines 35 and 45, delete formulas and insert in place thereof

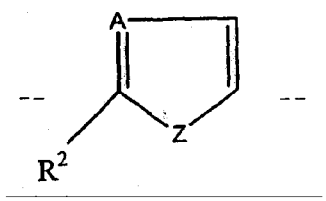

UNITED STATES PATENT AND TRADEMARK OFFICE
CERTIFICATE OF CORRECTION

PATENT NO.    : 6,602,900 B2
DATED         : August 5, 2003
INVENTOR(S)   : Robert M. Burk It is certified that error appears in the above-identified patent and that said Letters Patent is hereby corrected as shown below:

Column 40,
Lines 55 and 65, delete formulas and insert in place thereof

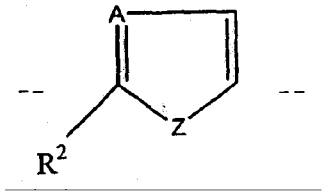

Signed and Sealed this

Ninth Day of March, 2004

JON W. DUDAS
*Acting Director of the United States Patent and Trademark Office*